(12) United States Patent
Dosdall et al.

(10) Patent No.: US 10,765,875 B2
(45) Date of Patent: Sep. 8, 2020

(54) IMPLANTABLE CARDIAC DEVICES AND METHODS FOR DELIVERING LOW ENERGY, PAIN-FREE DEFIBRILLATION SIGNALS FOR VENTRICULAR ARRHYTHMIAS

(71) Applicant: UNIVERSITY OF UTAH RESEARCH FOUNDATION, Salt Lake City, UT (US)

(72) Inventors: Derek J. Dosdall, Centerville, UT (US); Ravi Ranjan, Salt Lake City, UT (US)

(73) Assignee: UNIVERSITY OF UTAH RESEARCH FOUNDATION, Salt Lake City, UT (US)

( * ) Notice: Subject to any disclaimer, the term of this patent is extended or adjusted under 35 U.S.C. 154(b) by 0 days.

(21) Appl. No.: 15/971,883

(22) Filed: May 4, 2018

(65) Prior Publication Data

US 2018/0318594 A1 Nov. 8, 2018

Related U.S. Application Data

(60) Provisional application No. 62/501,693, filed on May 4, 2017.

(51) Int. Cl.
*A61N 1/39* (2006.01)
*A61N 1/37* (2006.01)

(52) U.S. Cl.
CPC ....... *A61N 1/39622* (2017.08); *A61N 1/3937* (2013.01); *A61N 1/3987* (2013.01); *A61N 1/3702* (2013.01)

(58) Field of Classification Search
CPC .............. A61N 1/39622; A61N 1/3987; A61N 1/3937; A61N 1/3702
See application file for complete search history.

(56) References Cited

U.S. PATENT DOCUMENTS 5,193,535 A 3/1993 Bardy et al.
5,257,621 A 11/1993 Bardy et al.
(Continued)

FOREIGN PATENT DOCUMENTS

WO WO 2012/054713 A1 4/2012

OTHER PUBLICATIONS

Allessie et al., "Regional control of atrial fibrillation by rapid pacing in conscious dogs," Circulation, 1991, 84:1689-1697.
(Continued)

*Primary Examiner* — Amanda K Hulbert
*Assistant Examiner* — Natasha Patel
(74) *Attorney, Agent, or Firm* — Michael Best & Friedrich LLP

(57) ABSTRACT

An implantable cardioverter defibrillator (ICD) and methods of detection and treatment of dangerous and life-threatening heart rhythms by delivering real-time, customized low-energy pacing pulses to specific anatomy in the heart. The ICD includes a power source, a controller, powered by the power source, including an electronic processor, a memory, and a signal generator. The ICD also includes a lead coupled to the controller and an electrode that is in electrical communication with a His-bundle of a patient's heart. The ICD detects a ventricular arrhythmia of the patient's heart using the controller, and is configured to provide a pulsed defibrillation signal to the electrode to terminate the ventricular arrhythmia.

8 Claims, 20 Drawing Sheets

(56) References Cited

U.S. PATENT DOCUMENTS

| | | | |
|---|---|---|---|
| 6,058,328 A * | 5/2000 | Levine | A61N 1/3622 607/14 |
| 7,027,866 B2 | 4/2006 | Warkentin | |
| 7,096,064 B2 | 8/2006 | Deno et al. | |
| 7,392,094 B2 | 6/2008 | Zhang et al. | |
| 7,457,664 B2 | 11/2008 | Zhang et al. | |
| 7,512,440 B2 | 3/2009 | Ortega et al. | |
| 7,643,876 B2 | 1/2010 | Zhang et al. | |
| 8,204,606 B2 | 6/2012 | Zhang et al. | |
| 8,761,880 B2 | 6/2014 | Maskara et al. | |
| 9,079,034 B2 | 7/2015 | Milbocker | |
| 2002/0120318 A1 | 8/2002 | Kroll et al. | |
| 2003/0233129 A1* | 12/2003 | Matos | A61B 5/0006 607/5 |
| 2004/0054380 A1 | 3/2004 | Craig et al. | |
| 2007/0260283 A1 | 11/2007 | Li | |
| 2008/0234771 A1 | 9/2008 | Chinchoy et al. | |
| 2010/0228330 A1 | 9/2010 | Bornzin | |
| 2011/0230922 A1* | 9/2011 | Fishel | A61N 1/3627 607/4 |
| 2012/0101539 A1* | 4/2012 | Zhu | A61N 1/0565 607/4 |
| 2013/0158621 A1 | 6/2013 | Ding et al. | |
| 2013/0261685 A1 | 10/2013 | Shuros et al. | |
| 2016/0106991 A1* | 4/2016 | Stadler | A61N 1/3987 607/5 |

OTHER PUBLICATIONS

Allison et al., "The transmural activation sequence in porcine and canine left ventricle is markedly different during long-duration ventricular fibrillation," J Cardiovasc Electrophysiol, 2007, 18:1306-1312.

Allred et al., "Transmural recording of shock potential gradient fields, early postshock activations, and refibrillation episodes associated with external defibrillation of long-duration ventricular fibrillation in swine," Heart rhythm: the official journal of the Heart Rhythm Society, 2008, 5:1599-1606.

Ambrosi et al., "Termination of sustained atrial flutter and fibrillation using low-voltage multiple-shock therapy," Heart rhythm: the official journal of the Heart Rhythm Society, 2011, 8:101-108.

Angel et al., "His bundle activates faster than ventricular myocardium during prolonged ventricular fibrillation," PLoS One, 2014, 9:e101666, 7 pages.

Arnar et al., "Purkinje involvement in arrhythmias after coronary artery reperfusion," Am J Physiol Heart Circ Physiol, 2002, 282:H1189-H1196.

Arnar et al., "Role of the purkinje system in spontaneous ventricular tachycardia during acute ischemia in a canine model," CIRC, 1997, 96:2421-2429.

Atkinson et al., "Anatomical and molecular mapping of the left and right ventricular his-purkinje conduction networks," J Mol Cell Cardiol, 2011, 51:689-701.

Barba-Pichardo et al., "Ventricular resynchronization therapy by direct His-bundle pacing using an internal cardioverter defibrillator," Europace, 2013, 15:83-88.

Bassett et al., "Chronic atrial fibrillation causes left ventricular dysfunction in dogs but not goats: Experience with dogs, goats, and pigs," Am J Physiol Heart Circ Physiol, 2013, 305:H725-731.

Bassett et al., "Evaluation of highly accelerated real-time cardiac cine mri in tachycardia," NMR in biomedicine, 2014, 27:175-182.

Bogun et al., "Role of purkinje fibers in post-infarction ventricular tachycardia," J Am Coll Cardiol, 2006, 48:2500-2507.

Borne et al., "Implantable cardioverter-defibrillator shocks: Epidemiology, outcomes, and therapeutic approaches," JAMA Intern Med, 2013, 173:859-865.

Bourland et al., "Sequential pulse defibrillation for implantable defibrillators," MEDINST, 1986, 20:138-142.

Boyden et al., "Nonuniform ca2+ transients in arrhythmogenic purkinje cells that survive in the infarcted canine heart," Cardiovasc Res, 2003, 57:681-693.

Boyle et al., "Purkinje-mediated effects in the response of quiescent ventricles to defibrillation shocks," Ann Biomed Eng, 2010, 38:456-468.

Butter et al., "Human experience with transvenous biventricular defibrillation using an electrode in a left ventricular vein," Pacing and clinical electrophysiology: PACE, 2002, 25:324-331.

Butter et al., "Transvenous biventricular defibrillation halves energy requirements in patients," Circulation, 2001, 104:2533-2538.

Cao et al., "Turbulence control with local pacing and its implication in cardiac defibrillation," Chaos, 2007, 17:015107, 9 pages.

Capucci et al., "Capture window in human atrial fibrillation: Evidence of an excitable gap," J Cardiovasc Electrophysiol, 1999, 10:319-327.

Catanzariti et al., "Permanent direct his bundle pacing does not induce ventricular dyssynchrony unlike conventional right ventricular apical pacing. An intrapatient acute comparison study," J Intery Card Electrophysiol, 2006, 16:81-92.

Catanzariti et al., "Permanent his-bundle pacing maintains long-term ventricular synchrony and left ventricular performance, unlike conventional right ventricular apical pacing," Europace, 2013, 15:546-553.

Cates et al., "Purkinje and ventricular contributions to endocardial activation sequence in perfused rabbit right ventricle," Am J Physiol Heart Circ Physiol, 2001, 281:H490-H505.

CDC, Centers for Disease Control and Prevention, "Heart Failure Fact Sheet," <https://www.cdc.gov/dhdsp/data_statistics/fact_sheets/fs_heart_failure.htm> webpage available since Jan. 25, 2011.

Cha et al., "Effects of chemical subendocardial ablation on activation rate gradient during ventricular fibrillation," Am J Physiol, 1995, 269:H1998-2009.

Chang et al., "Double and triple sequential shocks reduce ventricular defibrillation threshold in dogs with and without myocardial infarction," JACC, 1986, 8:1393-1405.

Chattipakorn et al., "Locally propagated activation immediately after internal defibrillation," CIRC, 1998, 97:1401-1410.

Chattipakorn et al., "Three-dimensional mapping of earliest activation after near-threshold ventricular defibrillation shocks," J Cardiovasc Electrophysiol. 2003, 14:65-69.

Cheek et al., "Nonlinear changes of transmembrane potential during electrical shocks: Role of membrane electroporation," Circulation research, 2004, 94:208-214.

Chen et al., "Current concepts of ventricular defibrillation," J Cardiovasc Electrophysiol, 1998, 9:553-562.

Coronel et al., "Laplacian electrograms and the interpretation of complex ventricular activation patterns during ventricular fibrillation," Journal of cardiovascular electrophysiology, 2000, 11:1119-1128.

Correa et al., "Autopsy analysis of the implantation site of a permanent selective direct his bundle pacing lead," Circ Arrhythm Electrophysiol, 2012, 5:244-246.

Csanadi et al., "Comparison of single-biphasic versus sequential-biphasic shocks on defibrillation threshold in pigs," PACE, 1997, 20:1606-1612.

Daoud et al., "F. Response of type i atrial fibrillation to atrial pacing in humans," Circulation, 1996, 94:1036-1040.

Daubert et al., "Inappropriate implantable cardioverter-defibrillator shocks in madit ii: Frequency, mechanisms, predictors, and survival impact," Journal of the American College of Cardiology, 2008, 51:1357-1365.

de Vreede-Swagemakers et al., "Out-of-hospital cardiac arrest in the 1990's: A population-based study in the maastricht area on incidence, characteristics and survival," J Am Coll Cardiol, 1997, 30:1500-1505.

Dobrzynski et al., "Structure, function and clinical relevance of the cardiac conduction system, including the atrioventricular ring and outflow tract tissues," Pharmacol Ther, 2013, 139:260-288.

Dosdall et al., "Chemical ablation of the purkinje system causes early termination and activation rate slowing of long-duration ventricular fibrillation in dogs," American journal of physiology. Heart and circulatory physiology, 2008, 295:H883-889.

(56) References Cited

OTHER PUBLICATIONS

Dosdall et al., "Differential electrograms computed from unipolar endocardial recordings improve purkinje activation identification," Computers in Cardiology, 2009, 36, 225-228.
Dosdall et al., "Effect of rapid biphasic shock subpulse switching on ventricular defibrillation thresholds," Journal of cardiovascular electrophysiology, 2004, 15:802-808.
Dosdall et al., "Guidelines for plunge needle recording for effective detection of purkinje activation," Conf Proc IEEE Eng Med Biol Soc, 2006, 1:3915-3918.
Dosdall et al., Mechanisms of defibrillation, Annu Rev Biomed Eng, 2010, 12:233-258.
Dosdall et al., "Purkinje activation precedes myocardial activation following defibrillation after long-duration ventricular fibrillation," Heart Rhythm, 2010, 7:405-412.
Dosdall et al., "Transmural and endocardial purkinje activation in pigs before local myocardial activation after defibrillation shocks," Heart Rhythm, 2007, 4:758-765.
Dosdall et al., Advances in mapping of ventricular fibrillation and defibrillation: Role of the purkinje system. In: Shenasa M, Hindricks G, Borggrefe M, Breithardt G, ME J, eds., Cardiac mapping Wiley-Blackwell, 2012.
Dura et al., "Spatiotemporally controlled cardiac conduction block using high-frequency electrical stimulation," PLoS One, 2012, 7:e36217, 9 pages.
Duytschaever et al., "Methods for determining the refractory period and excitable gap during persistent atrial fibrillation in the goat," Circulation, 2001, 104:957-962.
Estes et al., "Implantable cardioverter-defibrillators," 1994, 1-915.
Exner et al., "Combination biphasic waveform plus sequential pulse defibrillation improves defibrillation efficacy of a nonthoracotomy lead system," JACC, 1994, 23:317-322.
Eysmann et al., "Electrocardiographic changes after cardioversion of ventricular arrhythmias," Circulation, 1986, 73:73-81.
Fedorov et al., "Effect of electroporation on cardiac electrophysiology," Methods Mol Biol, 2008, 423:433-448.
Fishier, "Theoretical predictions of the optimal monophasic and biphasic defibrillation waveshapes," IEEE Trans Biomed Eng, 2000, 47:59-67.
Fitts et al., "Arrhythmia insensitive rapid cardiac t1 mapping pulse sequence," Magn Reson Med, 2013, 70:1274-1282.
Gintant et al., "Slow inactivation of a tetrodotoxin-sensitive current in canine cardiac purkinje fibers," Biophys J, 1984, 45:509-512.
Guse et al., "Defibrillation electrode configurations developed from cardiac mapping that combine biphasic shocks with sequential timing," AHJ, 1992, 124:1491-1500.
Guse et al., "Effective defibrillation in pigs using interleaved and common phase sequential biphasic shocks," PACE, 1993, 16:1719-1734.
Haissaguerre et al., "Role of purkinje conducting system in triggering of idiopathic ventricular fibrillation," LANC, 2002, 359:677-678.
Han et al., "Ionic remodeling of cardiac purkinje cells by congestive heart failure," Circulation, 2001, 104:2095-2100.
Hasdemir et al., "Analysis of troponin i levels after spontaneous implantable cardioverter defibrillator shocks," Journal of cardiovascular electrophysiology, 2002, 13:144-150.
Hayashi et al., "Novel mechanism of postinfarction ventricular tachycardia originating in surviving left posterior purkinje fibers," Heart Rhythm, 2006, 3:908-918.
Hicks et al., "The electrophysiology of rabbit hearts with left ventricular hypertrophy under normal and ischaemic conditions," Cardiovasc Res, 1995, 30:181-186.
Hirose et al., "Function of $Ca^{2+}$release channels in purkinje cells that survive in the infarcted canine heart: A mechanism for triggered purkinje ectopy," Circ Arrhythm Electrophysiol, 2008, 1:387-395.
Hosfeld et al., "A model for multi-site pacing of fibrillation using nonlinear dynamics feedback," J Biol Phys, 2007, 33:145-153.
Houser et al., "Animal models of heart failure: a scientific statement from the american heart association," Circ Res, 2012, 111:131-150.

Hsia et al., "Comparison of simulataneous versus sequential defibrillation pulsing techniques using a nonthoracotomy system," PACE, 1994, 17:1222-1230.
Hu et al., "Ligation of the left circumflex coronary artery with subsequent mri and histopathology in rabbits," Journal of the American Association for Laboratory Animal Science: JAALAS, 2010, 49:838-844.
Hu et al., "Magnetic resonance imaging (mri) assessment of ventricular remodeling after myocardial infarction in rabbits," Comparative medicine, 2012, 62:116-123.
Huang et al., "Ascending-ramp biphasic waveform has a lower defibrillation threshold and releases less troponin i than a truncated exponential biphasic waveform," Circulation, 2012, 126:1328-1333.
Huang et al., "Effect of electrode location in great cardiac vein on the ventricular defibrillation threshold," Pacing Clin Electrophysiol, 2002, 25:42-48.
Huang et al., "The importance of purkinje activation in long duration ventricular fibrillation," J Am Heart Assoc, 2014, 3:e000495, 16 pages.
Huang et al., "Ventricular defibrillation with triphasic waveforms," Circulation, 2000, 101:1324-1328.
Janardhan et al., "A novel low-energy electrotherapy that terminates ventricular tachycardia with lower energy than a biphasic shock when antitachycardia pacing fails," Journal of the American College of Cardiology, 2012, 60:2393-2398.
Janardhan et al., "Multistage electrotherapy delivered through chronically-implanted leads terminates atrial fibrillation with lower energy than a single biphasic shock," J Am Coll Cardiol, 2014, 63:40-48.
John Hopkins Medicine, "Results of Definitive Study Are In: Lives Are Saved When Defibrillators Are Placed in Large Public Spaces," <https://www.hopkinsmedicine.org/news/media/releases/results_of_definitive_study_are_in_lives_are_saved_when_defibrillators_are_placed_in_large_public_spaces> Release date: Nov. 5, 2007.
Johnson et al., "Adaptive pacing during ventricular fibrillation," Pacing Clin Electrophysiol, 2003, 26:1824-1836.
Johnson et al., "Effect of pulse separation between two sequential biphasic shocks given over different lead configurations on ventricular defibrillation efficacy," CIRC, 1992, 85:2267-2274.
Jones et al., "Biphasic versus sequential pulse defibrillation: A direct comparison in humans," AHJ, 1993, 125:405-409.
Jones et al., "Internal cardiac defibrillation in man: Pronounced improvement with sequential pulse delivery to two different lead orientations," CIRC, 1986, 73:484-491.
KenKnight et al., "Marked reduction of ventricular defibrillation threshold by application of an auxiliary shock to a catheter electrode in the left posterior coronary vein of dogs," J Cardiovasc Electrophysiol, 2000, 11:900-906.
KenKnight et al., "Regional capture of fibrillating ventricular myocardium. Evidence of an excitable gap," Circulation research, 1995, 77:849-855.
Kim et al., "Spatial distribution and extent of electroporation by strong internal shock in intact structurally normal and chronically infarcted rabbit hearts," Journal of cardiovascular electrophysiology, 2008, 19:1080-1089.
Kremers et al., "The national icd registry report: Version 2.1 including leads and pediatrics for years 2010 and 2011," Heart rhythm: the official journal of the Heart Rhythm Society, 2013, 10:e59-65.
Kroll et al., "Optimizing defibrillation waveforms for icds," J Interv Card Electrophysiol, 2007, 18:247-263.
Larsen et al., "Shocks burden and increased mortality in implantable cardioverter-defibrillator patients," Heart rhythm: the official journal of the Heart Rhythm Society, 2011, 8:1881-1886.
Lehmann et al., "Implantable cardioverter defibrillators in cardiovascular practice: Report of the policy conference of the north american society of pacing and electrophysiology. Naspe policy conference committee," Pacing Clin Electrophysiol, 1991, 4:211-220.
Li et al., "Activation becomes highly organized during long-duration ventricular fibrillation in canine hearts," Am J Physiol Heart Circ Physiol, 2010, 298:H2046-2053.

(56) References Cited

OTHER PUBLICATIONS

Li et al., "Defibrillation shocks produce different effects on purkinje fibers and ventricular muscle: Implications for successful defibrillation, refibrillation and postshock arrhythmia," Journal of the American College of Cardiology, 1993, 22:607-614.
Li et al., "Different types of long-duration ventricular fibrillation: Can they be identified by electrocardiography." J Electrocardiol, 2012, 45:658-659.
Li et al., "Long-duration ventricular fibrillation exhibits 2 distinct organized states," Circ Arrhythm Electrophysiol, 2013, 6:1192-1199.
Li et al., "Low-energy multistage atrial defibrillation therapy terminates atrial fibrillation with less energy than a single shock," Circ Arrhythm Electrophysiol, 2011, 4:917-925.
Lichter et al., "Remodeling of the sarcomeric cytoskeleton in cardiac ventricular myocytes during heart failure and after cardiac resynchronization therapy," J Mol Cell Cardiol, 2014, 74: 186-195.
Litwin et al., "Dyssynchronous ca(2+) sparks in myocytes from infarcted hearts," Circ Res, 2000, 87:1040-1047.
Litwin et al., "Enhanced na(+)-ca2+ exchange in the infarcted heart. Implications for excitation-contraction coupling," Circ Res, 1997, 81:1083-1093.
Luther et al., "Low-energy control of electrical turbulence in the heart," Nature, 2011, 475:235-239.
Masse et al., "K. Effect of global ischemia and reperfusion during ventricular fibrillation in myopathic human hearts. American journal of physiology," Heart and circulatory physiology, 2009, 297:H1984-1991.
Meisel et al., "Transvenous biventricular defibrillation," Am J Cardiol, 2000, 86:K76-K85.
Moe et al., "Alterations in serum sodium in relation to atrial natriuretic factor and other neuroendocrine variables in experimental pacing-induced heart failure," J Am Coll Cardiol, 1989, 13:173-179.
Mond et al., "The 11th world survey of cardiac pacing and implantable cardioverter-defibrillators: calendar year 2009—a World Society of Arrhythmia's project," Pacing Clin Electroophysiol, 2011, 34(8):1013-27.
Morgan et al., "Low energy defibrillation in human cardiac tissue: A simulation study," Biophys J, 2009, 96:1364-1373.
Myerburg et al., "Physiology of canine intraventricular conduction and endocardial excitation," Circulation research, 1972, 30:217-243.
Nakagawa et al., "Rapid high resolution electroanatomical mapping: Evaluation of a new system in a canine atrial linear lesion model," Circ Arrhythm Electrophysiol, 2012, 5:417-424.
Newton et al., "Pacing during ventricular fibrillation: Factors influencing the ability to capture," Journal of cardiovascular electrophysiology, 2001, 12:76-84.
Nogami et al., "Mapping and ablation of idiopathic ventricular fibrillation from the purkinje system," Heart Rhythm, 2005, 2:646-649.
O'Rourke et al., "Mechanisms of altered excitation-contraction coupling in canine tachycardia-induced heart failure, i: Experimental studies," Circ Res. 1999, 84:562-570.
Pak et al., "Both purkinje cells and left ventricular posteroseptal reentry contribute to the maintenance of ventricular fibrillation in open-chest dogs and swine," Circ J, 2008, 72:1185-1192.
Pak et al., "Improvement of defibrillation efficacy with preshock synchronized pacing," J Cardiovasc Electrophysiol, 2004, 15:581-587.
Pak et al., "Role of the posterior papillary muscle and purkinje potentials in the mechanism of ventricular fibrillation in open chest dogs and swine: Effects of catheter ablation," J Cardiovasc Electrophysiol, 2006, 17:777-783.
Pak et al., "Synchronization of ventricular fibrillation with real-time feedback pacing: Implication to low-energy defibrillation. American journal of physiology," Heart and circulatory physiology, 2003, 285:H2704-2711.
Pell et al., "Presentation, management, and outcome of out of hospital cardiopulmonary arrest: Comparison by underlying aetiology," HEART, 2003, 89:839-842.
Prabhu et al., "Effect of tachycardia heart failure on the restitution of left ventricular function in closed-chest dogs," Circulation, 1995, 91:176-185.
Prabhu, "Load sensitivity of left ventricular relaxation in normal and failing hearts: Evidence of a nonlinear biphasic response," Cardiovasc Res, 1999, 43:354-363.
Puwal et al., "Optimization of feedback pacing for defibrillation," IEEE Trans Biomed Eng, 2009, 56:532-534.
Qu et al., "Mechanisms of superiority of ascending ramp waveforms: New insights into mechanisms of shock-induced vulnerability and defibrillation," Am J Physiol Heart Circ Physiol, 2005, 289:H569-577.
Ranjan et al., "Diagnostic imaging and pacemaker implantation in a domestic goat with persistent left cranial vena cava," Journal of veterinary cardiology: the official journal of the European Society of Veterinary Cardiology, 2014, 16:45-50.
Rantner et al., "Terminating ventricular tachyarrhythmias using far-field low-voltage stimuli: Mechanisms and delivery protocols," Heart rhythm: the official journal of the Heart Rhythm Society, 2013, 1209-1217.
Roberts et al., "Reduction in defibrillation threshold using an auxiliary shock delivered in the middle cardiac vein," Pacing Clin Electrophysiol, 2000, 23:1278-1282.
Roberts et al., "Single capacitive discharge utilizing an auxiliary shock in the coronary venous system reduces the defibrillation threshold," J Intery Card Electrophysiol, 2001, 5:495-503.
Roberts et al., "The middle cardiac vein—a novel pathway to reduce the defibrillation threshold," J Interv Card Electrophysiol, 1999, 3:55-60.
Robertson et al., "Increased cycle length during long-duration ventricular fibrillation is caused by decreased upstroke velocity as well as prolonged refractoriness," Heart rhythm: the official journal of the Heart Rhythm Society, 2009, 6:378-384.
Robichaux et al., "Periods of highly synchronous, non-reentrant endocardial activation cycles occur during long-duration ventricular fibrillation," J Cardiovasc Electrophysiol, 2010, 21:1266-1273.
Robinson et al., "Electrical restitution process in dispersed canine cardiac purkinje and ventricular cells," Am J Physiol. 1987, 253:H1018-1025.
Sakaguchi et al., "Elimination of spiral chaos by pulse entrainment in the aliev-panfilov model," Phys Rev E Stat Nonlin Soft Matter Phys, 2005, 71:052901, 4 pages.
Sakaguchi et al., "Supression of spiral chaos bya a guiding network in teh aliev-panfilov model," Prog of Theor Phys Supp, 2006, 161:332-335.
Salama et al., "Subthreshold stimulation of purkinje fibers interrupts ventricular tachycardia in intact hearts. Experimental study with voltage-sensitive dyes and imaging techniques," Circulation research, 1994, 74:604-619.
Schwab et al., "Quantitative analysis of cardiac tissue including fibroblasts using three-dimensional confocal microscopy and image reconstruction: Towards a basis for electrophysiological modeling," IEEE transactions on medical imaging, 2013, 32:862-872.
Shaw et al., "Electrophysiologic effects of acute myocardial ischemia. A mechanistic investigation of action potential conduction and conduction failure," Circ Res, 1997, 80:124-138.
Shaw et al., "Electrophysiologic effects of acute myocardial ischemia: A theoretical study of altered cell excitability and action potential duration," Cardiovasc Res, 1997, 35:256-272.
Simon et al., "Effect of topic defibrillation on serum markers of myocardial damage," Interact Cardiovasc Thorac Surg, 2006, 5:75-77.
Steinhaus et al., "Pain perception of low energy shocks," Pacing Clin Electrophysiol, 2002, 25:1090-1093.
Szumowski et al., "Mapping and ablation of polymorphic ventricular tachycardia after myocardial infarction," J Am Coll Cardiol, 2004, 44:1700-1706.
Tabereaux et al., "Activation patterns of purkinje fibers during long-duration ventricular fibrillation in an isolated canine heart model," Circulation, 2007, 116:1113-1119.

(56) References Cited

OTHER PUBLICATIONS

Tandri et al., "Reversible cardiac conduction block and defibrillation with high-frequency electric field," Sci Transl Med, 2011, 3:102ra196, 9 pages.
Tang et al., "Post-shock synchronized pacing in isolated rabbit left ventricle: Evaluation of a novel defibrillation strategy," Journal of cardiovascular electrophysiology, 2007, 18:740-749.
Tang et al., "Three-dimensional potential gradient fields generated by intracardiac catheter and cutaneous patch electrodes," Circulation, 1992, 85:1857-1864.
Tokano et al., "Effect of ventricular shock strength on cardiac hemodynamics," Journal of cardiovascular electrophysiology, 1998, 9:791-797.
van Rees et al., "Inappropriate implantable cardioverter-defibrillator shocks: Incidence, predictors, and impact on mortality," Journal of the American College of Cardiology, 2011, 57:556-562.
Vijayaraman et al., "Imaging evaluation of implantation site of permanent direct his bundle pacing lead," Heart rhythm: the official journal of the Heart Rhythm Society, 2014, 11(3): 529-530.
Walker et al., "Critically timed auxiliary shock to weak field area lowers defibrillation threshold," J Cardiovasc Electrophysiol, 2001, 12:556-562.
Wang et al., "Electroporation induced by internal defibrillation shock with and without recovery in intact rabbit hearts," American journal of physiology. Heart and circulatory physiology, 2012, 303: H439-449.
Weinberg et al., "Defibrillation success with high frequency electric fields is related to degree and location of conduction block," Heart rhythm: the official journal of the Heart Rhythm Society, 2013, 10:740-748.
Wharton et al., "Cardiac potential and potential gradient fields generated by single, combined, and sequential shocks during ventricular defibrillation," Circulation, 1992, 85:1510-1523.
Winslow et al., "Mechanisms of altered excitation-contraction coupling in canine tachycardia-induced heart failure, ii: Model studies," Circ Res, 1999, 84:571-586.
Wu et al., "Ventricular fibrillation during no-flow global ischemia in isolated rabbit hearts," J Cardiovasc Electrophysiol, 2006, 17:1112-1120.
Xing et al., "Triggered activity due to delayed afterdepolarizations in sites of focal origin of ischemic ventricular tachycardia," Am J Physiol Heart Circ Physiol, 2004, 287:H2078-2084.
Young et al., "Combined cardiac resynchronization and implantable cardioversion defibrillation in advanced chronic heart failure: The miracle icd trial," Jama, 2003, 289:2685-2694.
Zanon et al., "A feasible approach for direct his-bundle pacing using a new steerable catheter to facilitate precise lead placement," Journal of cardiovascular electrophysiology, 2006, 17:29-33.
Zanon et al., "Direct his bundle and parahisian cardiac pacing," Ann Noninvasive Electrocardiol, 2012, 17:70-78.
Zheng et al., "Sudden cardiac death in the united states, 1989 to 1998," Circulation, 2001, 104:2158-2163.
Zhou et al., "Epicardial mapping of ventricular defibrillation with monophasic and biphasic shocks in dogs," Circulation research, 1993, 72:145-160.

\* cited by examiner

IMPLANTABLE CARDIAC DEVICES AND METHODS FOR DELIVERING LOW ENERGY, PAIN-FREE DEFIBRILLATION SIGNALS FOR VENTRICULAR ARRHYTHMIAS

CROSS-REFERENCE TO RELATED APPLICATION(S)

This application is a non-provisional of and claims the benefit of U.S. Provisional Patent Application Ser. No. 62/501,693, filed on May 4, 2017, the entire contents of which are incorporated herein by reference.

STATEMENT REGARDING FEDERALLY-SPONSORED RESEARCH OR DEVELOPMENT

This invention was made with government support under grant no. HL128752 awarded by the National Institutes of Health. The government has certain rights in the invention.

BACKGROUND OF THE INVENTION

Cardiovascular disease is the leading cause of death in most developed countries in the world. About half of all deaths from coronary heart disease are sudden and unexpected, regardless of the underlying disease. Approximately one million individuals in the U.S. develop conditions each year that place them at high risk for sudden cardiac death (SCD). About 450,000 SCDs occur each year among U.S. adults. Sudden Cardiac Arrest (SCA), the cause of SCD, is fatal in approximately 95% of cases. SCA often results from ventricular fibrillation (VF), which causes cardiac output to decrease nearly to zero, a level that causes irreversible damage to the brain and other organs within 10 min or less. Related to this fact, the odds of surviving SCA decrease approximately 10% for every minute the individual remains in VF before defibrillation is successfully performed. Patients at high risk for SCD may be implanted with an implantable cardioverter defibrillator (ICD) to provide life-saving defibrillation shocks in the event of the onset of a life-threatening cardiac arrhythmia. Approximately 150,000 patients receive ICD implantations each year in the U.S.

Current ICDs use high-energy (25-35 J) shocks to terminate VF. While large truncated exponential biphasic shocks used by modern devices are effective at terminating VF, the high current density surrounding shocking electrodes may cause tissue damage that leads to increased morbidity and mortality. This damage may be caused by electroporation, which leads to conduction disturbances, tissue stunning, necrosis, and compromised cardiac function. ICD shocks have been associated with elevated troponin I levels, a well-known marker of cardiac cell death. ICD patients that receive shocks are at an increased risk of death, even when shocks were delivered inappropriately for causes other than life-threatening arrhythmias. However, there is no increase in mortality risk in patients that received antitachycardia pacing but no shocks.

Severe mental distress and lower quality of life scores accompany many patients that receive defibrillation shocks. If a patient does not lose consciousness before a shock is delivered, large energy shocks cause severe pain. While ICD defibrillation shock strengths are often set at maximum levels of 35 J, shocks as low as 0.4 J are reported as painful. Inappropriate shocks are delivered to 11-13% of patients and the shocks are often delivered without warning. These patients are at increased risk for anxiety, stress, and possibly post-traumatic stress disorder.

ICDs charge a large capacitor to deliver defibrillation shocks, often up to hundreds of volts. Patients that receive multiple high-energy shocks deplete the battery of the ICD more rapidly, requiring expensive and invasive device replacement surgery. Development of reliable low energy defibrillation techniques will reduce the device size and prolong the battery life.

ICDs do not prevent the arrhythmias from occurring, but rather rapidly detect and treat the arrhythmias using electrical stimulation. Since the introduction of the ICD more than three decades ago, numerous improvements have been made to lower the energy required for cardioversion. Improvements to battery life and integrated electronics have shrunk the size of ICDs while increasing the longevity of the devices. Antitachycardia pacing (ATP) for ventricular tachycardia has reduced the number of shocks given for monomorphic VT episodes. However, ATP is not effective for VF. Biphasic shocks reduce the energy requirements and increase the success rates of defibrillation shocks. Alternate waveform shapes have had limited success in lowering defibrillation thresholds (DFTs), but have not been widely adopted and require shocks of sufficient amplitude that they cause damage and pain.

The critical mass theory of defibrillation states that for a defibrillation shock to be successful, a shock must render a critical mass (usually 75-90% of the ventricles) of the ventricular tissue unexcitable by activation or extension of the refractory period. Capturing large sections of cardiac tissue at sites distant from shocking electrodes is necessary to capture a critical mass of the heart and to terminate reentrant circuits that perpetuate VF. Cardiac mapping efforts during defibrillation have demonstrated that defibrillation attempts using a right ventricular electrode often fail because waves of activation emerge from the left ventricular apex region. This area of the left ventricle often has relatively low current density during the defibrillation shock. Several studies have explored the use of an auxiliary shock delivered to the LV electrode. Other studies have included the LV electrode as an additional path for current in parallel with other standard clinical locations. Since the LV electrode effectively spreads current into this area of low current density, DFTs drop significantly. While these techniques have lowered DFTs by as much as 50% or more, the DFTs are often still an order of magnitude above the pain threshold. Sequential pulses delivered through multiple pathways have not gained clinical acceptance due to additional complexity and risk associated with implantation of additional leads.

There has been a resurgence of interest and research into low energy multi-pulse and high frequency defibrillation techniques. These techniques generally fall into one of two categories: 1) A series of pacing pulses or low energy shocks delivered near or just below the intrinsic VF cycle length that progressively capture a larger and larger region of fibrillating tissue until VF is halted.22, 52-61 or 2) High frequency (50-1000 Hz) stimulation that blocks all activation in a critical mass so that reentrant circuits are disrupted and VF halts.

As with standard defibrillation shocks, low energy defibrillation techniques rely on far field virtual electrode polarization to create secondary sources that disrupt reentrant circuits to terminate VF. Traditional defibrillation shocks require a minimum field gradient of 2.7-10.9 V/cm throughout the heart for successful defibrillation. Intracardiac shocking coils, as used by ICDs, do not create an even field distribution throughout the heart. High current densities near shocking coils lead to field gradients more than 20 times the field gradient experienced by regions of the heart far from the shocking coils. While the field gradients required for multi-pulse techniques may be as low as 250 mV/cm, to create this field strength at sites distant from the shocking electrodes, much higher field gradients are required close to the shocking coils. Low energy multi-pulse techniques have been effective in simulations with even field gradients and in experimental configurations with rabbit or guinea pig ventricles or canine atria, but the energy required to defibrillate large, fibrillating ventricles with secondary sources at sites far from the stimulating electrodes will require substantial increases in energy and field gradient to create virtual electrodes at remote sites. Successful demonstration of low energy multi-pulse techniques in large hearts may prove difficult because direct local capture leads to a limited region of captured tissue, much smaller than a critical mass of the heart. While shocks from ICDs are the only effective therapy for VF, shocks may cause damage to tissue surrounding intracardiac electrodes leading to increased risk of arrhythmia or death. While the extent of the damage caused by shocks is controversial, shocks delivered while patients are conscious result in pain, anxiety, and lower quality of life measures.

SUMMARY OF THE INVENTION

The Purkinje system is a specialized conduction system that has been implicated as a source of idiopathic VF and selective radio frequency ablation of the Purkinje system has been used effectively to terminate and prevent idiopathic VT and VF. Studies have demonstrated that the Purkinje fiber system also may be responsible for the onset of arrhythmias during both ischemia and reperfusion, and that congestive heart failure (HF) leads to changes in the Purkinje cells that may make them more prone to arrhythmogenesis. Recent studies have demonstrated that radio frequency ablation of the endocardial posterior papillary muscle and the left ventricular posteroseptal region reduced the inducibility of VF in dogs.

Recent work has demonstrated that the Purkinje system plays an active role in the maintenance of VF. Mapping of the endocardium of isolated dog hearts showed that the Purkinje system plays an integral role in reentrant activity with the working myocardium and that focal activity in the Purkinje system initiates VF wavefronts. Chemical ablation of the Purkinje system led to slowing of VF activation rate and early spontaneous termination of VF. In later VF, a pattern of activation emerges during which the entire endocardium activates quickly through focal activity in the Purkinje system without activity on the endocardium between each cycle.

The Purkinje system has also been shown to be a possible source of activation leading to defibrillation shock failure when shocks are given near the DFT. DFT strength shocks induce rapid firing in the Purkinje system that may lead to shock failure. Purkinje activations have been detected before or during the postshock activation cycles in pig and dog hearts. Purkinje fibers and the intratrabecular gaps in which Purkinje fibers are found are common sites of virtual electrode effects, and thus are easily excited by shocks even when the underlying myocardium is not activated.

A recent study demonstrated that the His bundle activation rate was similar to that observed near the distal Purkinje fibers in prolonged VF. The study utilized isolated rabbit hearts (n=12) in which an 8×8 electrode array with 0.3 mm spacing was placed directly over the His bundle of isolated, perfused rabbit hearts. VF was induced with 50 Hz burst pacing, and perfusion was terminated. Shortly after VF onset, the working myocardium had a higher activation rate than the His bundle, but by the third minute of VF, the His activation rate was higher than that of the working myocardium (see FIG. 7). A repeated measures ANOVA demonstrated that the working myocardium activation rate decreased over time, while the His bundle activation rate did not change significantly over 8 minutes of VF. This behavior has been shown as an activation rate gradient that is observed in rabbits, dogs, and human hearts as the Purkinje system continues to activate rapidly while the working myocardium becomes ischemic and the activation rate slows away from the Purkinje-myocardial junctions. This study demonstrated that the His bundle exhibits similar activation patterns during VF, which indicates that the Purkinje system and His bundle remain electrically linked during VF and that pacing and capture of the His bundle will lead to capture of the Purkinje system during VF.

While there have been modeling or small animal heart studies that suggest that stimulating the Purkinje system during arrhythmias may lead to termination of the arrhythmias or reduction in energy required for termination, one obstacle to the clinical implementation of these techniques has been the lack of a clinically relevant method for stimulating the Purkinje system in vivo. Improved methods for pacing without causing ventricular dyssynchrony has driven a surge in research for directly pacing the ventricular conduction system.

Pacing the His bundle can be performed during an EP study with a steerable catheter placed on the high right ventricular septum. Recently, there have been several groups that have performed studies to validate techniques for placing a permanent pacing lead on the His bundle for chronic pacing applications. A small gauge steerable lead in conjunction with a steerable sheath have been positioned and fixed in location over the His bundle. Direct His bundle or paraHisian pacing leads to more synchronous contractions than a conventional right ventricular apical pacing. Of the patients that undergo dual lead implantation for cardiac resynchronization therapy (CRT), 30-40% of them do not show improvement in LV remodeling and/or reduced mortality. Some patients that are not candidates for traditional CRT therapy benefit from direct His bundle pacing. The end result of these studies is that permanent direct Hisian or paraHisian pacing techniques are gaining acceptance clinically and leads that are facilitate direct His pacing are commercially available.

According to an embodiment, the present invention provides an implantable cardioverter defibrillator (ICD) including a power source, a controller, powered by the power source, including an electronic processor, a memory, and a signal generator. The ICD also includes a lead coupled to the controller and an electrode that is in electrical communication with a His-bundle of a patient's heart. The ICD detects a ventricular arrhythmia of the patient's heart using the controller, and is configured to provide a pulsed defibrillation signal to the electrode to terminate the ventricular arrhythmia.

According to another embodiment, the present invention provides a method for ventricular defibrillation including detecting the presence of ventricular fibrillation in a patient via an implantable cardioverter-defibrillator having a controller electrically coupled to an electrode that is in electrical communication with a ventricular specialized conduction system of a patient's heart. The method also includes determining, via the controller, a ventricular fibrillation characteristic of a signal generated by the patient's heart, and determining, via the controller, a pulsed defibrillation signal including set of pacing pulse characteristics based on the ventricular fibrillation characteristic. Finally, the method includes delivering the pulsed defibrillation signal from the controller to the electrode in order to terminate the ventricular fibrillation.

According to yet another embodiment, the invention provides a method of treating a cardiac arrhythmia. The method comprises detecting, with an implanted device, a cardiac arrhythmia in a patient's heart, determining a characteristic of the cardiac arrhythmia, determining a signal to apply to the patient's heart, the signal including a set of timed small pulses based on the characteristic of the cardiac arrhythmia, and delivering the signal from the implanted device to an electrode in contact with a ventricular specialized conduction system of the heart to terminate the cardiac arrhythmia.

In a further embodiment, the invention provides an implantable cardioverter-defibrillator comprising a power source, a controller, powered by the power source, including an electronic processor, a memory, and a pulse generator, a His-bundle lead coupled to the controller and an electrode that is in electrical contact with the His-bundle of a patient's heart, and a sensing lead coupled to the controller and in electrical communication with the patient's heart, the sensing lead configured to detect electrical signals generated by the patient's heart. The controller is configured to receive the electrical signals provided by the sensing lead, process the electrical signals to determine if ventricular fibrillation is present, if ventricular fibrillation is detected on the electrical signals, transmit instructions to the pulse generator to deliver a pulsed defibrillation signal to the electrode to terminate the ventricular fibrillation.

Other features and aspects of the invention will become apparent by consideration of the following detailed description and accompanying drawings.

DETAILED DESCRIPTION

Figure 1:
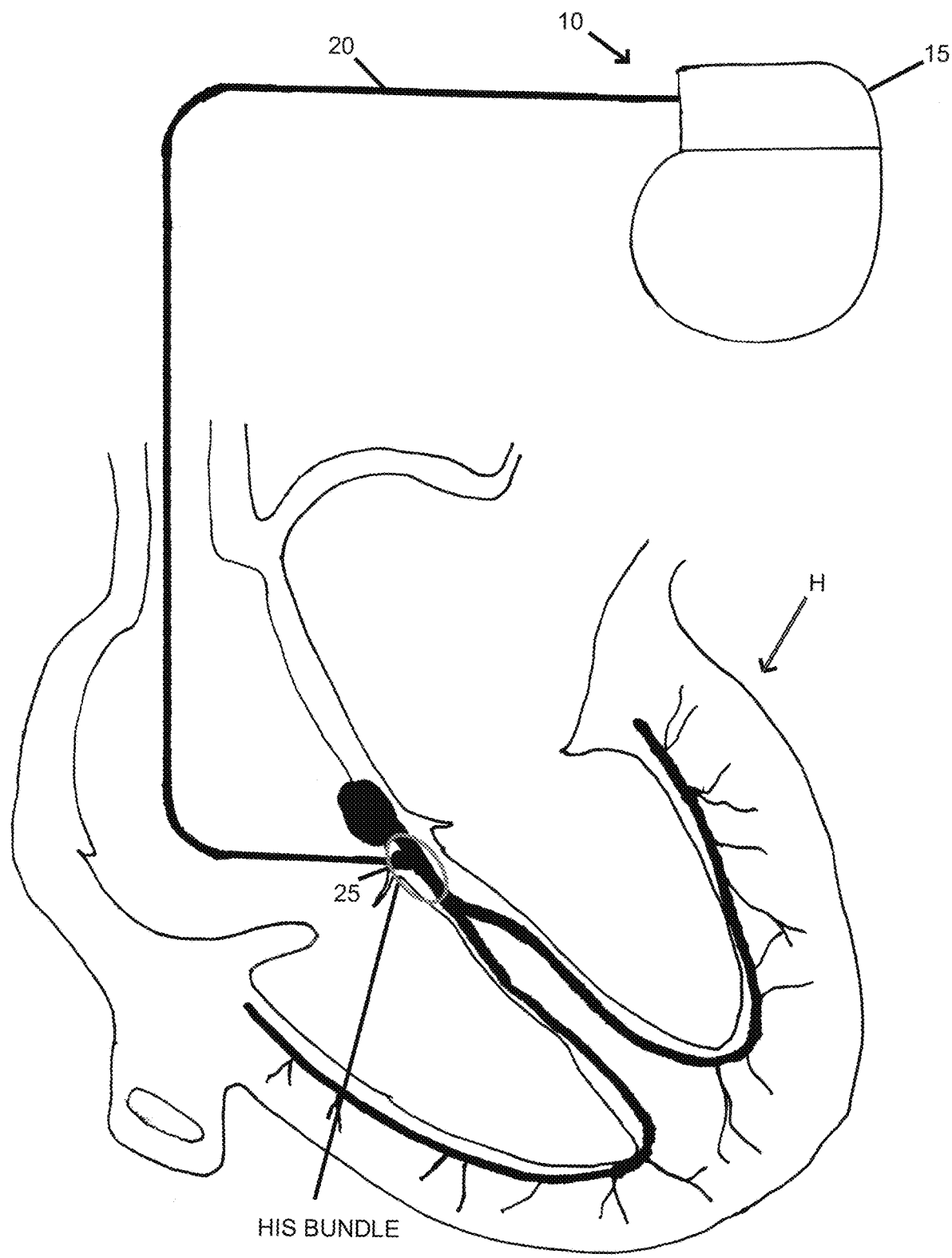
FIG. 1 is a representation of an implantable cardioverter defibrillator having a lead disposed within a patient's heart.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways.

Also, it is to be understood that the phraseology and terminology used herein is for the purpose of description and should not be regarded as limiting. The use of "including," "comprising" or "having" and variations thereof herein is meant to encompass the items listed thereafter and equivalents thereof as well as additional items. The terms "mounted," "connected" and "coupled" are used broadly and encompass both direct and indirect mounting, connecting and coupling. Further, "connected" and "coupled" are not restricted to physical or mechanical connections or couplings, and may include electrical connections or couplings, whether direct or indirect. Also, electronic communications and notifications may be performed using any known means including direct connections, wireless connections, etc.

It should also be noted that a plurality of hardware and software based devices, as well as a plurality of different structural components, may be used to implement various embodiments described herein. In addition, it should be understood that embodiments may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic based aspects may be implemented in software (e.g., stored on non-transitory computer-readable medium) executable by one or more processors. As such, it should be noted that a plurality of hardware and software based devices, as well as a plurality of different structural components may be utilized to implement various embodiments. Furthermore, and as described in subsequent paragraphs, the specific configurations illustrated in the drawings are intended to exemplify embodiments and that other alternative configurations are possible. For example, "controllers" described in the specification can include standard processing components, such as one or more processors, one or more computer-readable medium modules, one or more input/output interfaces, and various connections (e.g., a system bus) connecting the components. In some instances, the controllers described in the specification may be implemented in one of or a combination of a general processor, an application specific integrated circuit (ASIC), a digital signal processor (DSP), a field programmable gate array (FPGA), combinational logic or state circuitry, or the like.

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are hereby incorporated by reference in their entirety. The materials, methods, and examples disclosed herein are illustrative only and not intended to be limiting.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

"About" is used synonymously herein with the term "approximately." Illustratively, the use of the term "about" indicates that values slightly outside the cited values, namely, plus or minus 10%. Such values are thus encompassed by the scope of the claims reciting the terms "about" and "approximately."

The present disclosure provides a novel ICD for detecting and terminating cardiac arrhythmias and method of using the same. The device as described herein improves detection and treatment of dangerous and life-threatening heart rhythms by delivering real-time, customized low-energy pacing pulses to specific anatomy in the heart. Additionally, the low-energy pacing pulses provide a pain free treatment to the patient in contrast to conventional large, mono-phasic or biphasic defibrillation shocks that are typically painful for the patient.

FIGS. 1-6 illustrate an exemplary implantable cardioverter defibrillator (ICD) 10 configured to detect and terminate arrhythmias (e.g., ventricular fibrillation (VF), ventricular tachycardia, etc.). The ICD 10 includes a housing 15 configured to be implanted into a patient (e.g., within the thoracic cavity remote spaced from the patient's heart) having one or more leads 20 extending from the housing into the interior of the heart H via one or more veins. As described in greater detail below, the ICD 10 is configured to execute a method in order to detect and treat VF using low-energy pacing pulses delivered to the ventricular specialized conduction system, e.g., His bundle, and propagated through the ventricles via the Purkinje fibers in order to terminate VF by rendering a critical mass of ventricular tissue unexcitable by activation thereby terminating reentrant circuits that perpetuate VF. Accordingly, normal sinus rhythm can be restored using low-energy pacing pulses rather than conventional large, mono-phasic or biphasic defibrillation shocks.

With reference to FIG. 1, the ICD 10 includes a lead 20 extending from the housing 15 to an electrode 25 coupled to the ventricular specialized conduction system of the patient's heart. The ventricular specialized conduction system includes the His bundle, bundle branches, and the Purkinje system. More particularly, in other embodiments, the electrode is coupled to the His-bundle in the patient's heart. The ICD 10 also includes a sensing lead extending from the housing 15 and into the heart for sensing and detecting ventricular arrhythmias, in particular, ventricular fibrillation. The sensing lead provides a signal to the ICD for processing and determination of next steps as described below.

In other embodiments, the ICD 10 may include two or more leads 20 having corresponding electrodes. The additional leads may include, but are not limited to, an additional His-bundle lead that includes an electrode that is coupled to the His-bundle (i.e., another His-bundle electrode) within the patient's heart H, one or more right atrial leads with an electrode that is coupled at a point within the right atria or onto the myocardium of the right atria (i.e., right atrial electrode), one or more right ventricular leads with an electrode that is coupled at a point within the right ventricle or onto the myocardium of the right ventricle (i.e., right ventricular electrode), one or more left atrial leads with an electrode that is coupled at a point within the left atria or onto the myocardium of the left atria (i.e., left atrial electrode), and one or more left ventricular leads with an electrode that is coupled at a point within the left ventricle or onto the myocardium of the left ventricle (i.e., right atrial electrode).

Figure 2:
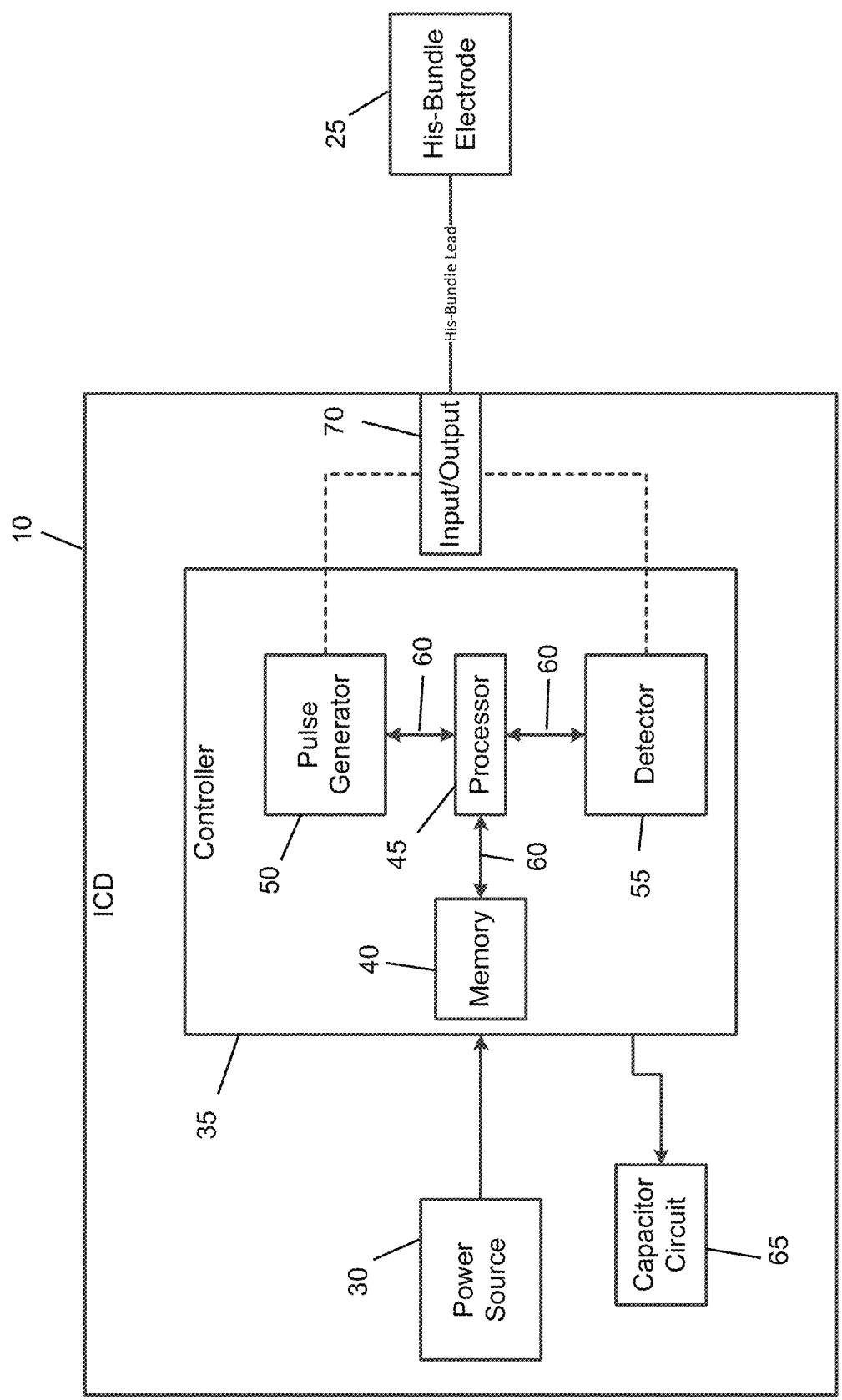
FIG. 2 illustrates a block diagram of the ICD of FIG. 1.

FIG. 2 illustrates an exemplary block diagram of the ICD 10. As illustrated, the ICD 10 includes a plurality of electrical and electronic components that provide power, operational control, and protection to the components and modules within the device. The ICD 10 includes a power supply 30 (e.g., a battery) for powering a controller 35 having a memory 40, an electronic processor 45, a pulse generator 50, a detector circuit 55, coupled by a bus 60. The ICD 10 also includes a capacitor circuit 65 for delivering a defibrillation shock to the heart H or cardiac tissue. The device 10 may also include additional or alternative components, including additional electronic processors and memory, or application specific integrated circuits (ASICs).

The controller 35 executes software, which may be stored in the memory 40, via the electronic processor 45 to carry out the functionalities of the ICD 10. The electronic processor 45 is communicatively coupled to the memory 40 and executes instructions stored on the memory 40. The electronic processor 45 is configured to retrieve from the memory 40 and execute, among other things, instructions related to the control processes and methods described below.

The memory 40 stores program instructions and data. The memory 40 may include, for example, a program storage area and a data storage area. The program storage area and the data storage area may include combinations of different types of memory, such as read-only memory ("ROM"), random access memory ("RAM") (e.g., dynamic RAM ["DRAM"], synchronous DRAM ["SDRAM"], etc.), electrically erasable programmable read-only memory ("EEPROM"), flash memory, or other suitable magnetic, optical, physical, or electronic memory devices.

The pulse generator 50 and the detector circuit 55 are each coupled to the electronic processor 45 and an input/output port 70 configured to receive the His-bundle lead 25 such that the pulse generator 50 and detector circuit 55 are in electrical communication with the His-bundle electrode 25. In other embodiments, the pulse generator 50 and the detector circuit 55 may be coupled to additional data input/output ports 70 that are configured to receive the additional leads described above such that the pulse generator 50 and the detector circuit 55 are in electrical communication with the corresponding electrodes of the leads.

The pulse generator 50 may be any suitable electronic circuit, ASIC, etc. configured to provide electrical pulses having specific characteristics (e.g., pulse frequency, pulse duration, pulse voltage, pulse current, etc.). The detector circuit 55 may be any suitable circuit, ASIC, hardware, or software configured to obtain, detect, and/or pre-process electrical signals from the heart provided by the sensing wire 22. In addition, the detector circuit 55 may be embodied in software, executable by the electronic processor 45, for the functions described herein.

In some embodiments, the ICD 10 further includes a communication module (e.g., a transceiver) that couples the ICD to a peripheral device (e.g., a server, computer, tablet, smartphone, etc.) via a communication link to enable the controller to communicate with the peripheral device. The communication link may include one or more wired or wireless connections, networks, and protocols including, but not limited to a local area network (LAN), the Internet, Wi-Fi, cellular, LTE, 3G, Bluetooth, Ethernet, USB, and the like. In one example, the communication module may allow a user to access or update software stored in the memory via data transmitted from a peripheral device to the communication module. In another example, the controller may be configured to send data gathered by the electronic processor and stored in the memory via the communication module for peripheral processing and analysis.

Figure 3A:
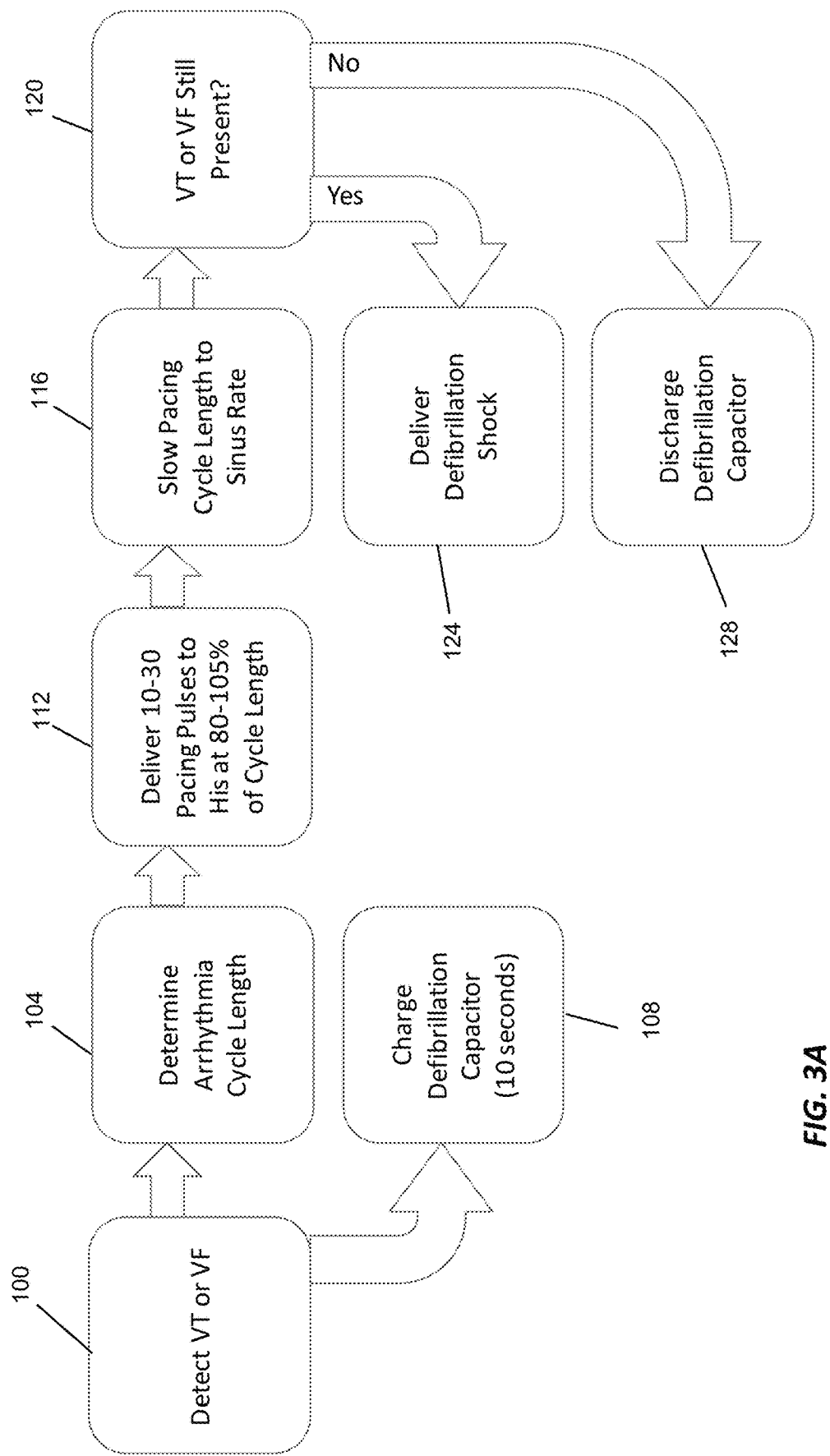
FIG. 3A is a flow chart illustrating a method for treating a cardiac arrhythmias using the ICD of FIG. 1.

FIG. 3A is a flow chart illustrating a method for treating a cardiac arrhythmia. The method includes the controller 35 sampling electrical signals (via the sensing lead) propagating through the heart (step 100) to determine whether or not an arrhythmia, such as VF or VT is present based on the sample electrical signal. If a cardiac arrhythmia is present in the sample electrical signal, the controller 35 executes (at step 104) an algorithm for the signal to determine a cycle length of the arrhythmia and a set of pacing pulse characteristics for the arrhythmia. The cycle length of the arrhythmia can be determined via known software methodology that resides in existing ICDs. In addition (at step 108), a defibrillation capacitor 65 in the ICD 10 is charged for a period of time (e.g., 10 seconds). Based on the cycle length of the arrhythmia, the controller 35 generates a defibrillation pulse signal, which is subsequently communicated to the pulse generator 50 to generate and transmit the defibrillation pulse signal to the His-bundle electrode 25 via the His-bundle lead 20 (step 112) to accomplish defibrillation. For example, the pulse generator 50 can deliver 5-30 pacing pulses to the His-bundle at 50-105% of the cycle length of the arrhythmia. As another example, the pulse generator 50 can deliver 10-25 pacing pulses to the His-bundle at 80-105% of the cycle length of the arrhythmia. The pulse generator 50 then slows (at step 116) the delivery of the pacing pulses of the cycle length to the sinus rate. The controller 35 again samples (at step 120) electrical signals propagating through the heart to determine whether or not an arrhythmia, such as VF or VT is present based on the sample electrical signal. If the cardiac arrhythmia is still present, the controller 35 transmits (at 124) a signal to the capacitor circuit 65 to deliver a defibrillation shock to the cardiac tissue. If the cardiac arrhythmia is no longer present in the sample electrical signal, the controller 35 transmits (at 128) a signal to the capacitor circuit 65 to discharge the capacitor. It is noted that these low energy cardioversion techniques (e.g., with the parameters noted above) delivered directly to the His-bundle to capture the Purkinje system have not previously been shown to be effective in halting VF.

Figure 3B:
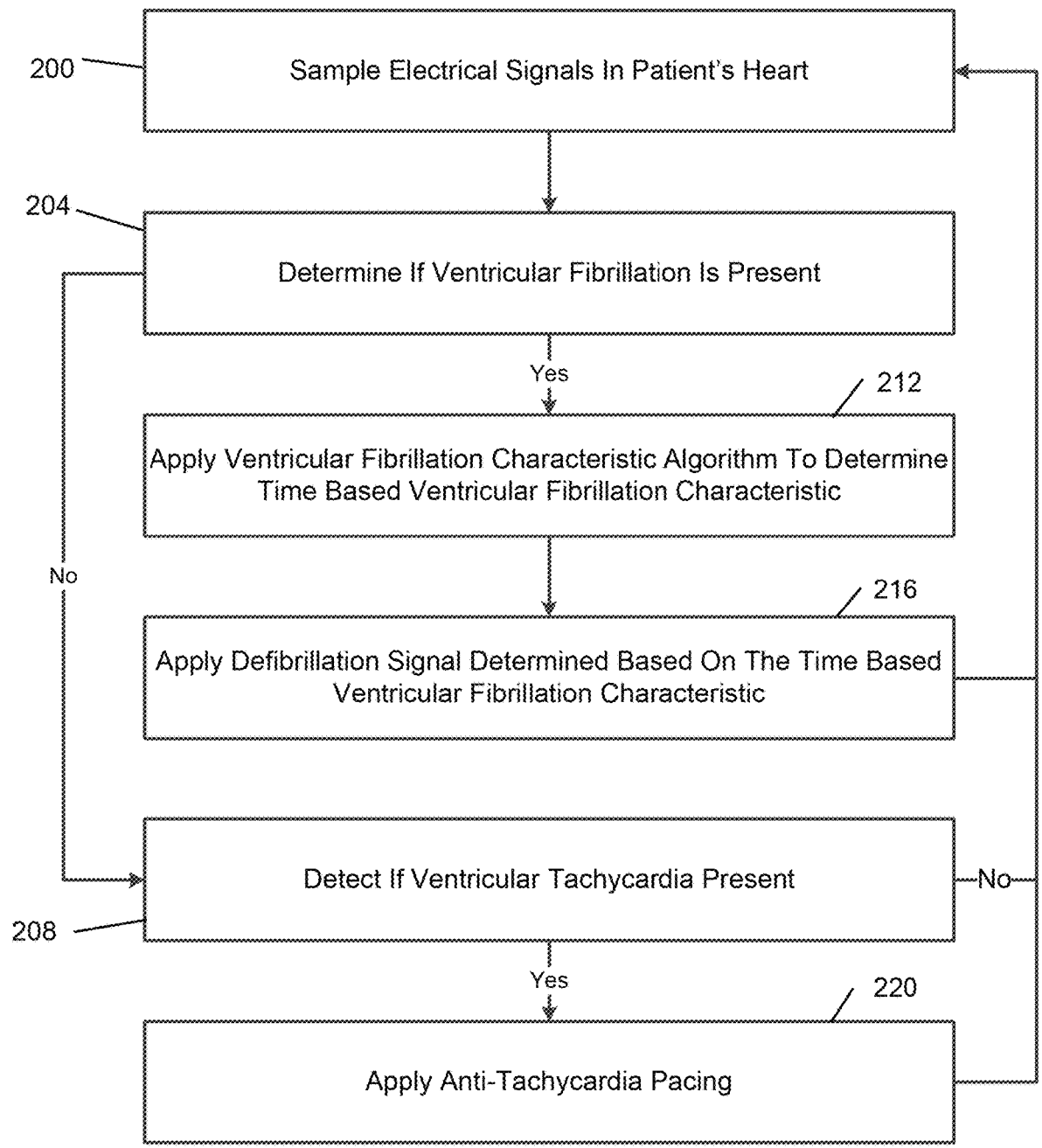
FIG. 3B is a flow chart illustrating a method for terminating ventricular arrhythmias using the ICD of FIG. 1.

FIG. 3B illustrates one method for detecting and terminating ventricular arrhythmias using the ICD 10. The method includes sampling electrical signals propagating through the heart (step 200), determining whether or not VF is present based on the sample electrical signal (step 204), and determining whether or not VT is present based on the sample electrical signal (step 208). If VF is present in the sample electrical signal, the controller 35 executes (at step 212) a VF characteristic algorithm to the signal to determine a set of pacing pulse characteristics for a defibrillation signal, which is subsequently communicated to the pulse generator 50 to generate and transmit the defibrillation pulse signal to the His-bundle electrode 25 via the His-bundle lead 20 (step 216) to accomplish defibrillation. After defibrillation, the ICD 10 returns to step 200. If VF is not present in the sample electrical signal, but VT is present, the controller 35 is configured to communicate conventional ATP signal characteristics to the pulse generator 50, which subsequently generates and transmits an ATP signal to the His-bundle electrode 25 via the His-bundle lead 20 (step 220). If neither VF nor VT is present in the sample electrical signal, the controller 35 continues to continuous or timed repetition of step 200 (i.e., sampling of the electrical signals propagating through the heart). In addition, it should be apparent that VT may be present or induced by the defibrillation signal, making ATP necessary after defibrillation in order to recapture normal sinus rhythm.

The sampling accomplished in step 200 more specifically includes operating the ICD 10 to sample the electrical signals propagating through the heart H. The sample electrical signal is gathered, for example, as a change in voltage at the His-bundle electrode over time that is pre-processed by the detector circuit 55 and delivered to the electronic processor 45. Subsequently, the sample electrical signals are processed by the electronic processor 45 to determine intrinsic characteristics of the heart H over time such as heart rate/cycle length, and rate comparison (i.e., rate of the ventricles compared to the rate of the atria), among others. The intrinsic characteristics may be stored to the memory 40 to create a record of heart functionality. Subsequently, the electronic processor 45 evaluates the intrinsic characteristics to determine whether the sample electrical signals are indicative of VF or VT. For example, the electronic processor 45 may make a comparison of the signal to known VF or VT patterns stored in the memory 40 to determine if ventricular fibrillation is present.

Figure 4:
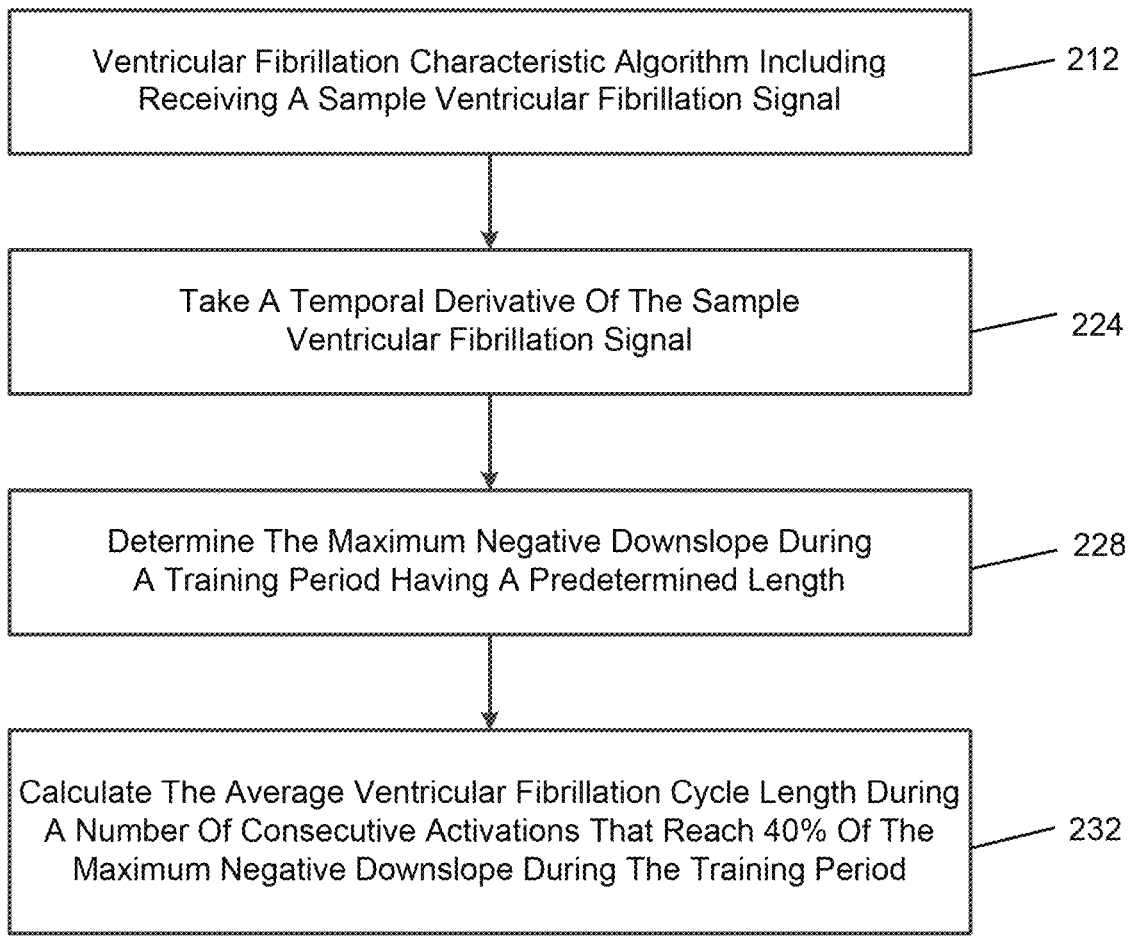
FIG. 4 is a flow chart of a method for determining a characteristic of ventricular fibrillation.

With reference to FIG. 4, step 212 more specifically includes executing, via the electronic processor 45, a VF characteristic algorithm that is stored in the memory to determine a time based VF characteristic (e.g., ventricular fibrillation cycle length, ventricular fibrillation cycle rate, etc.) after VF is detected in step 204. In the illustrated embodiment, the VF characteristic algorithm includes receiving a sample VF electrical signal, taking (at step 224) a temporal derivative of the sample VF electrical signal, determining (at step 228) the maximum negative downslope during a training period having a predetermined length, and calculating (at step 232) the average VF cycle length during a number of consecutive activations that reach 40% of the maximum negative downslope during the training period. Accordingly, the VF characteristic algorithm uses the sample VF electrical signal to determine an average VF cycle length. Alternatively, other algorithms for determining average VF cycle length, or other VF time based characteristics, may be employed.

Figure 5:
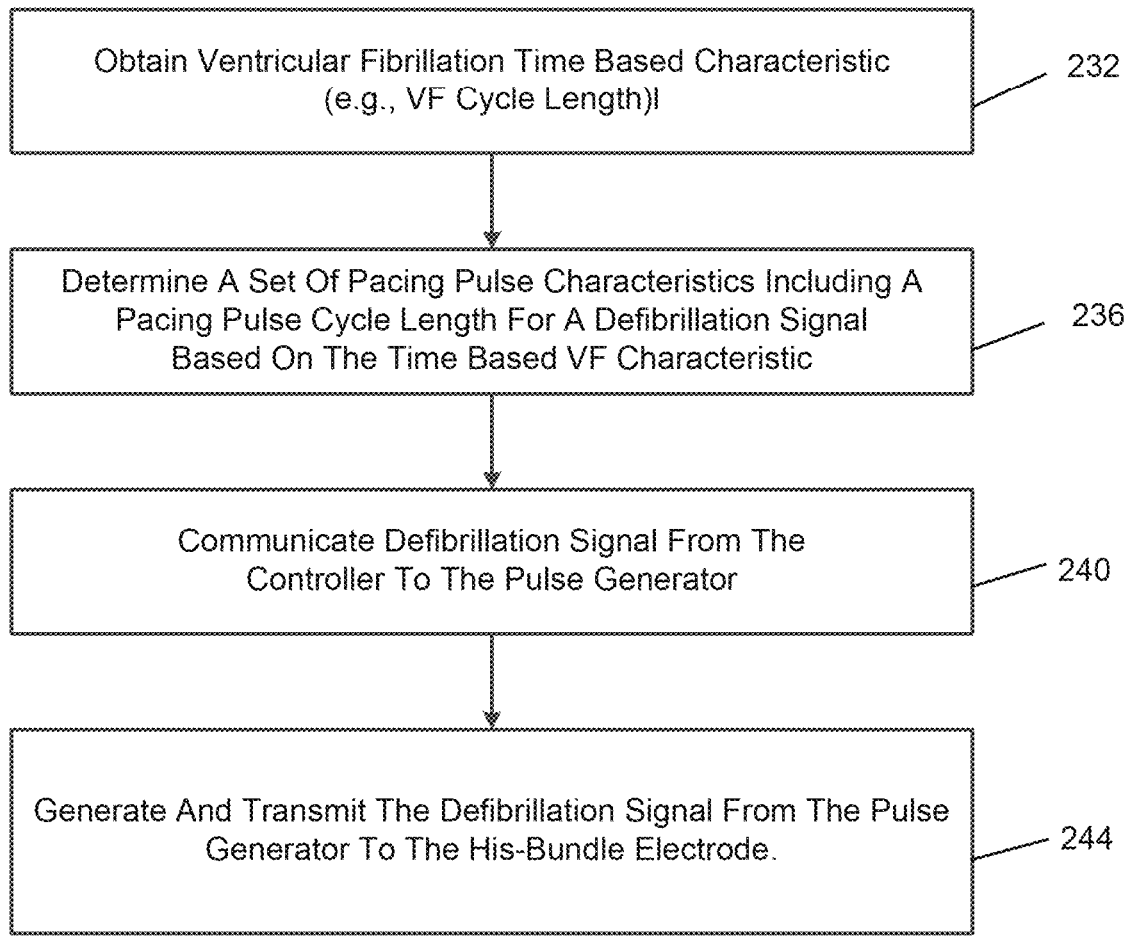
FIG. 5 is a flow chart of a process for terminating ventricular fibrillation using the ICD of FIG. 1.

With reference to FIG. 5, step 232 more specifically includes executing, via the electronic processor 45, a VF treatment algorithm to determine (at step 236) a set of pacing pulse characteristics (e.g., number of pulses, pulse duration, cycle length, current, voltage, etc.) for the defibrillation signal based on the average VF cycle length. In the illustrated embodiment, the set of pacing pulse characteristics may set a pacing pulse cycle length that is between approximately 50-105% of the VF cycle length. More specifically, the pacing pulse cycle length may be approximately 90% of the VF cycle length. In this example, the number of pulses, pulse duration, pulse voltage, and pulse current may be predetermined values (e.g., based on patient characteristics, etc.) or functions (e.g., successively increasing/decreasing pulse duration or pulse voltage, etc.). However, the number of pulses, the pulse duration, pulse voltage, and pulse current may also be varied based on the VF cycle length. In addition, when other VF time-based characteristics determined in the method, the set of pacing pulse characteristics may be either varied or set as predetermined values.

With continued reference to FIG. 5, the controller 35 subsequently communicates (at step 240) the defibrillation signal to the pulse generator 50, which in turn generates and transmits (at step 244) the defibrillation signal to the His-bundle electrode 25 via the His-bundle lead 20 using power from the power supply 30.

Step 208 more specifically includes communicating the ATP signal characteristics from the controller 35 to the pulse generator 50 after VT is detected. The pulse generator 50 then generates and transmits an ATP signal to the His-bundle electrode 25 via the His-bundle lead 20.

In operation, the ICD 10 detects and terminates arrhythmias (e.g., according to the methods of FIGS. 3A and 3B). The ICD 10 monitors electrical activity within the heart H to detect the presence of VF and VT, and subsequently delivers a treatment upon detection. When VF is detected, the ICD 10 delivers the defibrillation signal in order to terminate VF. In the example described above, the defibrillation signal includes a set of pacing pulse characteristics having the pacing pulse cycle length that is between approximately 70-98% of the sampled VF cycle length. Delivery of this defibrillation signal to the His-bundle via the His bundle electrode 25, which is illustrated in the exemplary waveform of FIG. 6, has specific physiological implications for terminating VF.

Delivery of the defibrillation signal to the His-bundle results in the electrical signal being propagated through the ventricles via the Purkinje fibers. When delivered at the pacing pulse cycle length, each successive pulse's propagation through the ventricles results in recapture of increasing amounts of synchronous depolarization of successive portions of cardiac tissue prior to improper, asynchronous depolarization of portions of ventricular tissue due to fibrillation. Once a critical mass of cardiac tissue is captured and depolarization is propagated properly through the critical mass of cardiac tissue, fibrillation is considered to be terminated and the ventricles will contract such that blood flow is restored.

Figure 6:
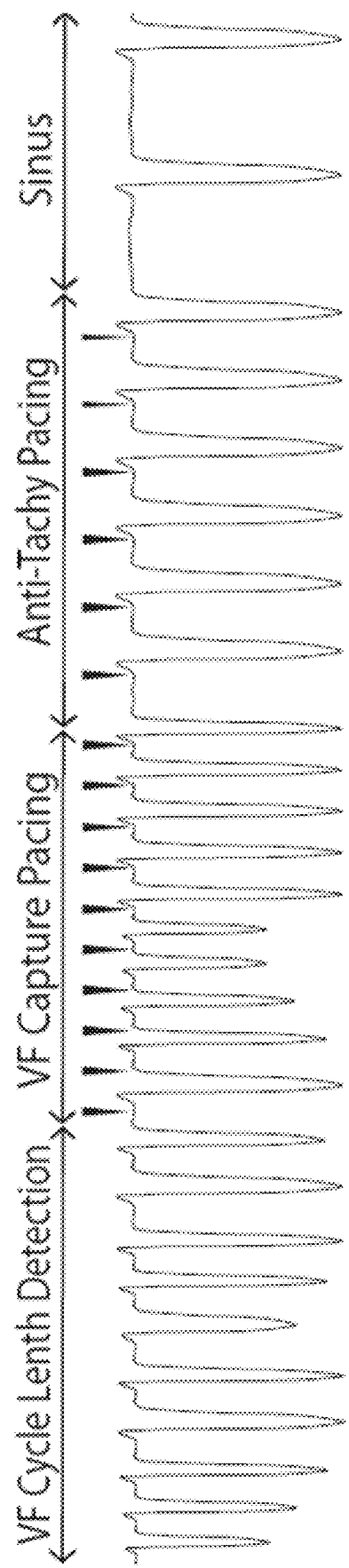
FIG. 6 is an exemplary electrocardiogram depicting implementation of the process of FIG. 3.
Figure 7:
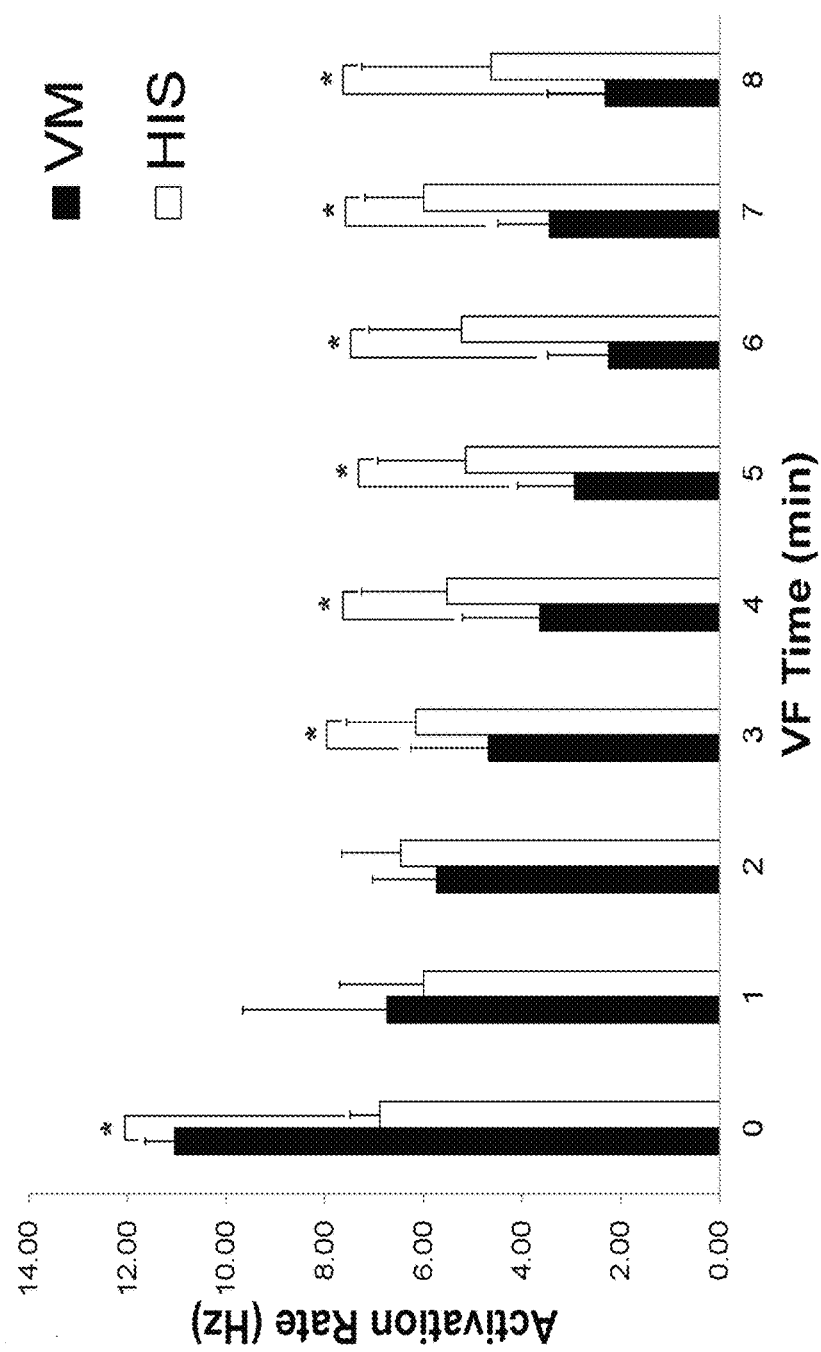
FIG. 7 is a chart that illustrates that an activation rate gradient develops between the His bundle and the underlying ventricular myocardium (VM) as VF progresses. At VF onset, the VM activation rate is higher than the His bundle activation rate. From the 3rd minute of VF on, the His bundle activation rate is faster than that of the VM. Significance shown with * for p<0.05 with Bonferroni-Holm correction.

In some cases, such as the exemplary waveform illustrated in FIG. 6, VT is induced or occurs after defibrillation. Accordingly, after defibrillation is accomplished, VT is detected resulting in the application of ATP to terminate VT and restore sinus rhythm.

Advantageously, the stepwise recapture of cardiac tissue via the Purkinje fiber conduction pathway obviates the necessity for a high magnitude shock in order to terminate fibrillation. The pacing pulse cycle and each pulse's subsequent propagation through the His-bundle significantly decrease the energy required to accomplish defibrillation. This results in decreased cardiac tissue morbidity due to high magnitude shocks, decreased pain experienced by patients during defibrillation, a reduction in anxiety associated with prior ICD's defibrillation techniques, and an overall increase in ICD patients' quality of life.

EXAMPLES

The overall goal is to combine three new concepts and techniques into a clinically relevant method for low energy defibrillation. As discussed above, the key concepts that have formed embodiments of the invention are: 1) low energy multi-pulse defibrillation techniques have demonstrated the feasibility of substantial reductions in shock energy in simulations and small hearts, 2) the Purkinje system plays an active role in the maintenance of VF and in defibrillation shock failure, and 3) development of methods for directly pacing the Purkinje system with clinically relevant, permanent leads. The combination of these three independent breakthroughs will lead to significant reductions in DFTs.

Example 1: The Purkinje System can Operate as a Pacing Distribution System During VF Such that Cardiac Activation May Spread Through the Conduction System and Capture Sufficient Cardiac Mass Such that VF Wavefronts are Halted This approach has the potential to reduce DFTs to a series of pacing level amplitude shocks. This approach is fundamentally different from traditional defibrillation mechanisms. Effective defibrillation therapy has been based on the principle that large shocks not only directly stimulate tissue near the shocking electrodes, but that virtual electrode effects cause secondary sources at sites far from the shocking electrodes. Substantial reductions in defibrillation energy are unlikely to be achieved while the primary mechanism for defibrillation is the creation of secondary sources far from stimulating electrodes. Since this technique is based on local capture and spread of activation through the conduction system rather than creation of far field secondary sources, the stimulation energy requirements will be comparable to pacing-level energies, which are well tolerated by patients and do not result in cardiac damage. This may result in orders of magnitude reductions in defibrillation energy, thereby resulting in damage free, painless defibrillation that can be performed with current pacemaker and ICD technology.

Since the intended treatment population for this technology is patients with ICDs, the techniques were developed and demonstrated first in normal rabbit and dog hearts, but then will also be tested in infarcted rabbit hearts with heart failure (HF) and in dogs with HF and cardiomyopathy.

Many animal models of HF are available, each with strengths and weaknesses. For testing the proposed low energy cardioversion techniques, several concerns are: 1) distribution and function of the conduction system, 2) representative model of the ICD population, and 3) feasibility of use within the budget and capabilities available. As noted above, rabbits and dogs have a similar Purkinje fiber distribution to humans. Patients with ICDs have compromised LVEF, often with ischemic heart disease and dilated cardiomyopathy. For these reasons, both a rabbit ischemic HF model and a canine rapid ventricular paced HF model will be utilized. While these models do not represent all ICD patients, the combination of these two models represents a large contingent of ICD patients.

While dogs, sheep, and pigs have been used for rapidly paced dilated cardiomyopathy, dogs offer the most similar conduction system to humans and have been well characterized. The inventors have extensive experience with chronic pacing AF models and have implanted and tracked approximately 50 dog and goat animals in AF. Even with beta-blockers to slow the ventricular response rate, dogs undergoing rapid atrial pacing develop LV dysfunction and HF (LVEF decreased from 54% at baseline to 33% after 6 months of AF). As a pilot study, RV leads were implanted and RV pacing was conducted at 240 beats per minute for 3 weeks followed by 220 beats per minute and achieved significant HF in a goat model. These goats developed enlarged hearts and compromised EF, consistent with dilated cardiomyopathy.

In order to utilize the Purkinje system as a pacing distribution system in VF, the Purkinje system must have an excitable gap, as does the working myocardium. At normal sinus heart rates, the Purkinje system has a longer APD and thus longer refractory period than the working myocardium. However, under rapid pacing rates, the APD and refractory periods of the Purkinje system accommodate to the rapid rates such that Purkinje fibers have the same or shorter APDs and refractory periods than cardiomyocytes.

The His bundle, bundle branches, and even many of the proximal Purkinje fibers are electrically isolated from the underlying myocardium. The more rapid conduction velocity of the Purkinje system (1.5-4 m/s) compared to the working myocardium (0.3-0.5 m/s) combined with the lack of electrical continuity with the underlying myocardium would suggest that large sections of the His-Purkinje system should activate synchronously during VF. It was previously demonstrated that the Purkinje system is an interactive player in the re-entrant and focal activity that occurs during VF and during defibrillation.

Myocardial ischemia has been shown to affect APD and post-repolarization refractoriness. An excitable gap in normal conduction tissue and myocardium may not indicate that the same will be true in chronic infarct tissue. There is often a layer of subendocardial sparing associated with infarct, and the excitability of this tissue is unknown compared to the surrounding tissue during VF.

In a first study, rabbit hearts were excised, perfused, and opened. An incision was made through the anterior RV and through the anterior septum to expose the LV endocardium. A rigid plastic ring attached to a rod was sutured over the high left bundle branch (LBB) on the LV septum. The ring was held in place to minimize motion of the tissue under the ring. A bipolar electrode on a micromanipulator was used to identify the LBB bundle and was used to directly pace the His bundle. Floating microelectrodes were used to impale the LBB as well as the adjacent ventricular working myocardium. VF was induced electrically and allowed to stabilize in the perfused heart for 30 seconds. This simulated early VF and minimized the time effect as global ischemia set in in an unperfused VF model. Action potential duration (APD) and diastolic interval (DI) were quantified for the LBB and adjacent working myocardium. The VF activation rate of the LBB was determined, and pacing pulses were delivered from the electrode set closest to the Purkinje fiber impalement site for 2 seconds at the VF cycle length. Following a 10 second recovery period, trains lasting 2 seconds were delivered at 5% intervals below the VF cycle length (at 95, 90, 85, . . . 55, 50% of the Purkinje fiber VF cycle length), with 10 second recovery periods between tests. Post-repolarization refractoriness and the excitable gap in the LBB and working myocardium were determined by comparing minimum cycle lengths that result in capture, action potential characteristics, and coupling intervals to pacing pulses.

Figure 8:
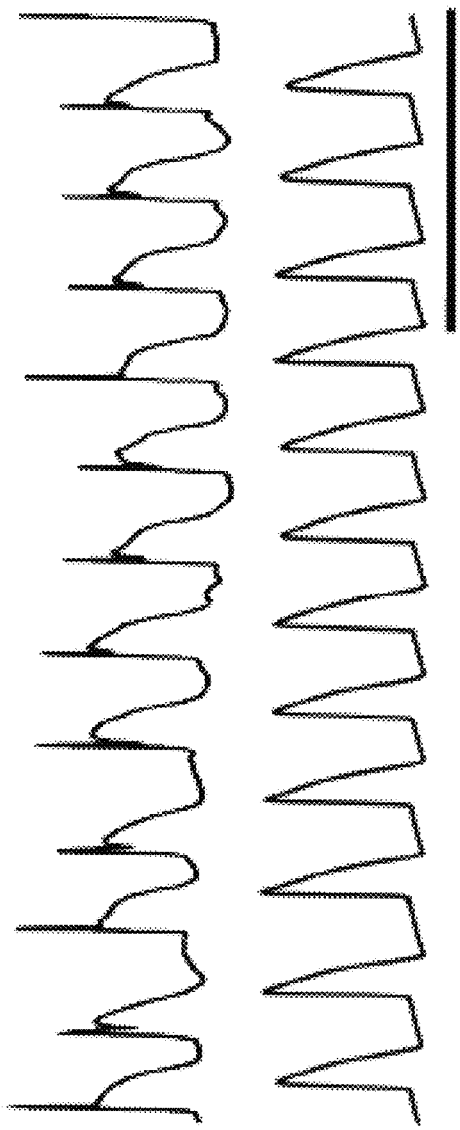
FIG. 8 illustrates microelectrode recordings from a Purkinje fiber (top trace) and adjacent working myocardium (lower trace) during VF in an isolated canine heart. Horizontal bar at the bottom shows 500 ms. The Purkinje impalement has a more notable spike and dome.

Preliminary studies demonstrate the ability to record simultaneous microelectrode recordings from the endocardium of a fibrillating heart (FIG. 8). While these recordings were obtained in a dog heart with a microelectrode in a free running Purkinje fiber and adjacent myocardium, the technique was similar for His bundle and myocardial impalement in the rabbit heart.

Figure 9:
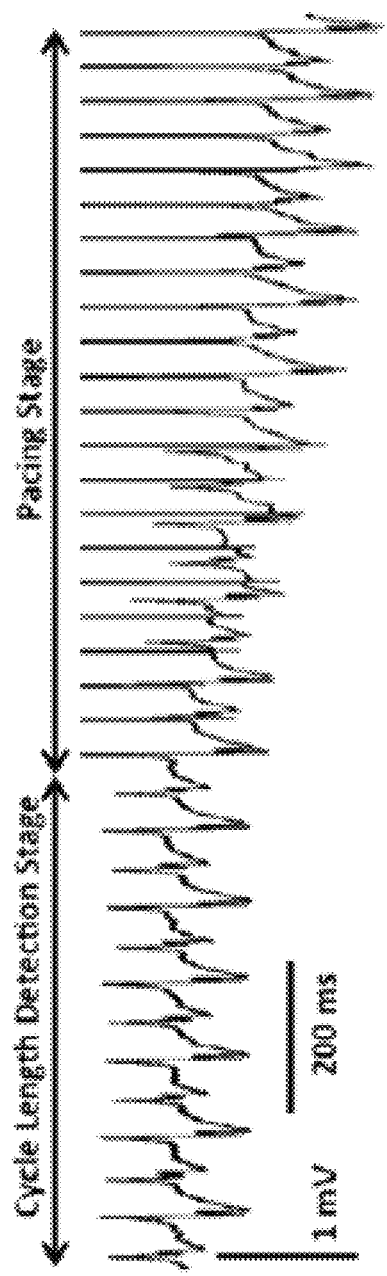
FIG. 9 illustrates that the VF activation rate was detected for 13 cycles (mean activation rate=48.4 ms) followed by a pacing train delivered at 90% of the mean activation rate (pulse every 43.5 ms). Following approximately 10 activation cycles, the pacing captures a section of local myocardium.

An experiment was conducted with an isolated rabbit heart to demonstrate the ability to perform real time rate detection and pacing delivery. An analog input of a digital signal processor microcontroller board (TMS320C5516 16 bit fixed point 100 MHz process with a 24 bit ADC, Texas Instruments, Inc.) was used to record an electrogram from a hook electrode on the LV epicardium of an isolated and perfused rabbit heart. A pacing electrode (approximately 3 mm from the sensing electrode) was inserted into the LV free wall epicardium. The heart was put into fibrillation with burst pacing. The microcontroller took the temporal derivative of the sensing electrode, determined the maximum negative downslope during a 4 second training period, calculated the average cycle length during 13 consecutive activations that reached 40% of the maximum negative downslope during the training period, and delivered 10-50 pacing pulses at 90% of the average VF cycle length. The pacing pulses were able to capture a section of fibrillating myocardium in the vicinity of the pacing electrode during VF (FIG. 9).

Figure 10:
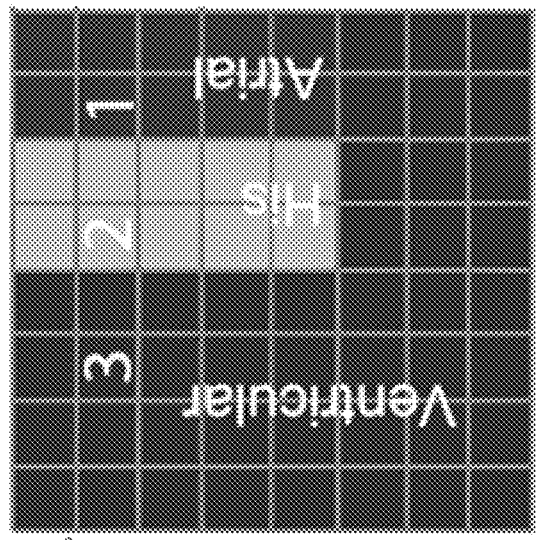
FIG. 10 illustrates an array placed over the His bundle of an isolated rabbit heart. A strong ventricular, His, and atrial signals were recorded during sinus rhythm from the 3 regions of the plaque shown in red, green, and blue, respectively. Electrograms at sites 1, 2, and 3 are shown in FIG. 11.
Figure 11:
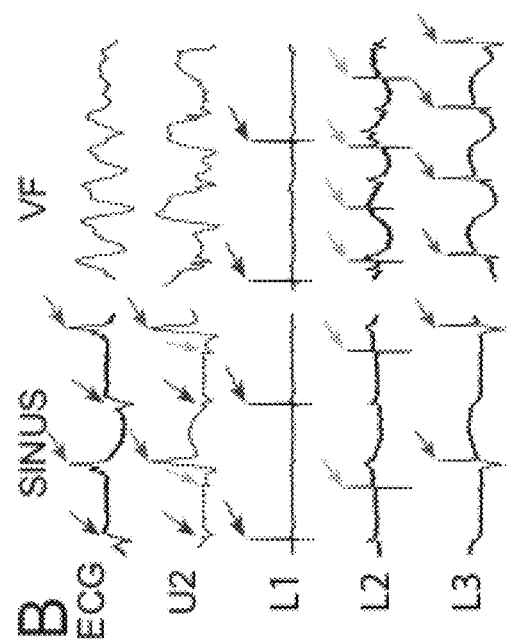
FIG. 11 illustrates a pseudo ECG, unipolar electrogram (from site 2 in FIG. 10), and 3 Laplacian recordings (from sites 1, 2, and 3 in FIG. 10) during sinus and VF. Each recording was 500 ms in duration. The unipole at site 2 shows ventricular (red arrows), His bundle (green arrows), and atrial (blue arrows) deflection, while the Laplacians isolate the strongest local signal and eliminate far field signals. During VF, it is difficult to distinguish different activation types with the unipolar signal, but the Laplacians facilitate waveform identification.

The ability to differentiate His bundle activation from the working myocardium during VF was demonstrated. An 8×8 array with 0.6 mm spacing was placed over the His bundle and sinus and VF were recorded. While the unipolar recordings were sufficient to identify His-bundle activations during sinus rhythm, bipolar and Laplacian (4*center electrode—N, S, E, W electrodes) electrograms reduced far field signals and improved local signal detection (FIGS. 10-11). With the Laplacian electrograms, Ventricular, His-bundle, and atrial activations could easily be distinguished during VF.

Figure 12:
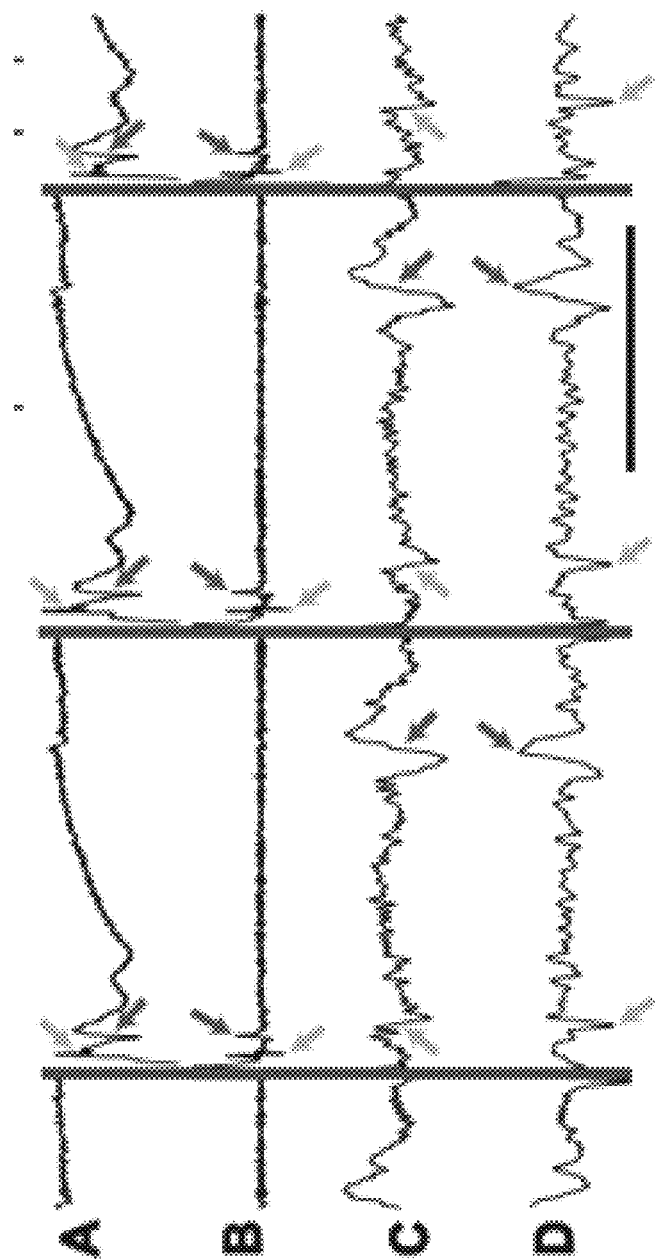
FIG. 12 illustrates pacing the His bundle during VF with 2 mA leads to Purkinje and myocardial capture. Pacing artifacts (purple lines), His-Purkinje activations (green arrows), and myocardial activations (red arrows) are shown. Horizontal bar shows 100 ms. (A) Laplacian electrogram and (B) its temporal derivative at a site 1.2 mm from the pacing site shows both His and myocardial capture. (C) Laplacian and (D) its temporal derivative at a site 1.5 cm from pacing site demonstrate propagation of both the Purkinje potential and myocardial activation during VF.

In an isolated rabbit heart, the His bundle was identified as in FIG. 12. A second array was placed on the RV septal endocardium in a region approximately 1-2 cm from the His bundle array. Perfused VF was induced electrically, and then pacing pulses were delivered to the His bundle at 95% of the intrinsic His-bundle activation rate. Pacing at 2 mA captured the His bundle near the pacing site as well as Purkinje and myocardial tissue 1-2 cm from the His site (see FIG. 12). This experiment demonstrated that 1) an excitable gap exists in the Purkinje system during VF, and 2) pacing can capture not only the local His, but that the paced impulse can travel to sites distant from the paced site through the conduction system during VF.

Example 2: Effective Pacing Parameters for Terminating VF Through Pacing of the His-Purkinje System Multi-pulse defibrillation techniques that deliver stimuli near the VF cycle length rely on progressive capture of increasing amounts of tissue with a train of pulses. Low energy multi-pulse defibrillation techniques may be effective in large hearts if one or more of the following criteria are met: 1) pulses are of sufficient strength to cause virtual electrodes at sites distant from the stimulation electrodes, 2) pulses are delivered at strategic locations such that stable reentrant circuit sites are disrupted and the pacing pulses can dominate the activity of the heart, or 3) excitation pulses are distributed throughout much of the heart such that tissue captured adjacent to electrodes sums to a critical mass of the heart and extinguishes activity throughout the heart. Criteria 1 is utilized by clinically accepted defibrillation techniques. Very large shocks are almost always nearly successful in terminating fibrillation, but due to reasons outlined earlier, reductions in defibrillation thresholds would lead to less pain, damage, and device longevity. Criteria 2 has proven to be problematic because there does not seem to be a consensus as to critical anatomical or functional locations that would be consistent, predictable targets for stable reentrant circuits. Criteria 3 would either require a very large number of electrodes throughout much of the heart, which would not be clinically acceptable, or utilization of the specialized conduction system to spread activation pulses through much of the heart in a nearly synchronously. Embodiments of the invention utilize the ventricular specialized conduction system of the heart to distribute pacing pulses through a large area of the heart to capture a critical mass of the heart and to thereby terminate VF.

As noted above, several different multi-pulse algorithms have been published. High frequency AC techniques are likely to rely on direct stimulation of the tissue to cause conduction block. An alternative technique is based on the same principles used to pace sections of the myocardium during fibrillation. These techniques typically involve calculating the mean VF cycle length and then delivering pacing pulses at or just below the VF cycle length. Pacing at 95% of the VF cycle length captured a mean of 3.8 cm$^2$ of the epicardium in a pig VF model. The region of tissue captured by pacing increased in size until the stimulus current reached approximately 10 times the diastolic pacing threshold. Anti-tachycardia pacing, which delivers a series of pacing pulses at a cycle length shorter than the inherent cycle length of ventricular tachycardia, is often successful at stopping tachycardia, but rarely terminates VF. It is noted that these studies have not applied these techniques to the His bundle or the ventricular specialized conduction system of the heart. In the studies, these techniques have not been applied to the His bundle because research published by the inventors' labs has only recently led to understanding the important role that the His-Purkinje system plays in VF maintenance. The inventors of this pioneering work in identifying the critical role of the specialized ventricular conduction system led to the innovative approach of interfacing the His-Purkinje system directly to distribute critically timed pulses to the rest of the myocardial tissue. Also, until recently, there has not been a clinically relevant method for interfacing the His bundle directly. However, with the emergence of techniques for placing a permanent His bundle electrode for resynchronization and pacing therapy gaining traction in the cardiac electrophysiology community and with our unique understanding of the His-Purkinje system in VF, this novel approach was developed for low energy and pain free termination of VF.

Since a single electrode can effectively capture a section of tissue, multiple electrodes have been used to attempt to capture a broader region of tissue. Four pacing electrodes configured to pace during the excitable gap on the surface of an isolated rabbit heart successfully defibrillated the heart in 16% of VF episodes. Simulations have recommended optimal spacing and timing of pacing pulses through multiple electrodes. Little interest in placing electrodes throughout the heart has blunted interest in this technique.

A multistage defibrillation approach has been shown to lower defibrillation energy requirements. A first phase consisting of relatively large monophasic or biphasic shocks is thought to unpin wavefronts in fibrillation. The second phase of medium amplitude shocks prevents wavefronts from repining. The third phase is essentially ATP and is thought to annihilate any remaining wavefronts. Investigators have used this multiphase approach to terminate VT and atrial fibrillation in a canine model. Recent studies have shown that multistage defibrillation trains lowered the AF DFT from 1.48 J to a cumulative 0.16 J in rapid atrial pacing induced AF dogs when comparing standard biphasic shocks to multistage defibrillation, respectively.

Recent modeling work has sought to determine the most effective parameters for multistage defibrillation techniques. A high resolution MM scan was used to reconstruct a model of a rabbit RV. Sustained VF was established and shocks from far-field electrodes were simulated. Stimuli were delivered at 16% and 88% of the VF cycle length. Pulses delivered at 88% of the VF cycle length were more effective than those delivered at 16%. VF was regularly converted to either sinus rhythm or VT at 0.58% of the energy that was required with single defibrillation shocks. Further reductions in energy were achieved when VF was converted to VT and ATP pacing was employed. In this simulation, stimuli delivered at 88% of the VF cycle length terminated VF with only 2-3 times the diastolic activation threshold.

Low energy multi-pulse defibrillation techniques have been shown to be effective in small animal models and simulation, but efficacy in treating large animals in VF has not been published. This is likely due to the inability of the small shocks to create virtual electrodes at sites far from the pacing site. Low energy multi-pulse defibrillation therapy has been delivered through standard pacing electrodes placed in the RV endocardial apex, on the LV epicardium through CRT leads in the cardiac venous system, or in open chest models with multiple electrodes placed on the ventricular epicardium, but clinically relevant lead placement is highly limited in both location and number of electrodes. Local pacing may capture several cm$^2$ of tissue during VF, which may be sufficient to terminate VF in a small heart, such as a rabbit or guinea pig heart, but this is not sufficient to terminate VF in a large heart such as a dog, pig, or human heart.

Previous work has demonstrated that wavefronts in the Purkinje system during VF may be large and that myocardial activation is often initiated by wavefronts in the Purkinje system. Since the conduction velocity is much faster in the Purkinje system than in the working myocardium, the pacing pulses spread throughout a much larger region during the excitable gap than they did in working myocardial cells. Pacing at the His bundle lead to rapidly spreading excitation wavefronts that progressively captured larger and larger sections of the working myocardium throughout the ventricular mass.

Many patients with an ICD have dilated cardiomyopathy and HF. Ion channel remodeling, increased fibrosis, increased myocardial mass, electrical remodeling, and other effects may change the Purkinje-myocardial coupling or VF characteristics. Therefore, the experiments were conducted in both normal hearts and rapid paced dilated cardiomyopathy HF dog hearts to determine if these changes affect the efficacy of direct His-Purkinje pacing.

Figure 13:
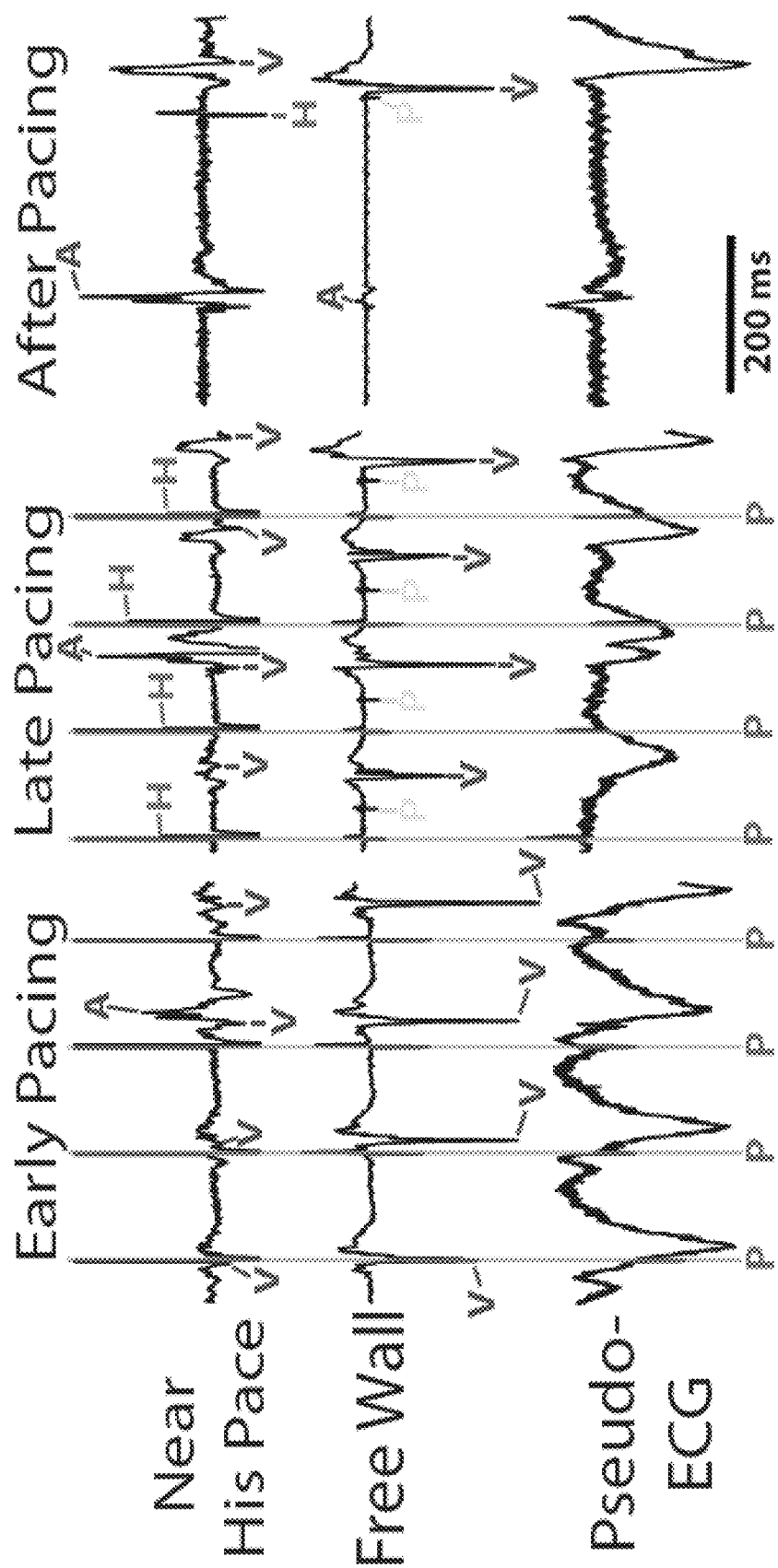
FIG. 13 illustrates His bundle pacing leads to His, Purkinje, and ventricular myocardial capture as well as VF termination. Electrogram recordings from an electrode near the His pacing site (0.3 mm away), from a separate plaque located on the apical RV free wall, and from a pseudo-ECG from an isolated rabbit heart in perfused VF. Each recording is 500 ms in duration. The His activation rate was detected and 30 pacing pulses were delivered at 90% of the His VF cycle length. Ventricular myocardial (V), His bundle (H), atrial (A), Purkinje activations (P), and stimulation pacing (S) are marked. Immediately after beginning pacing (Early Pacing), there is no evidence of His, Purkinje, nor myocardial capture. After approximately 20 pacing cycles (Late Pacing), His capture occurs almost immediately following the pacing stimulus with 1:1 ventricular activations. On the free wall, there is a repeatable delay before Purkinje activation, followed by a phase locked myocardial activation. Myocardial activation was earlier at the free wall than near the His pacing site, which is consistent with activation proceeding from the His bundle to the Purkinje fibers, to the working myocardium near the Purkinje fibers, and finally to the myocardium near the His pacing site. After termination of pacing, VF is terminated, although there was a period of AV conduction block or delay before sinus rhythm recommenced.
Figure 14:
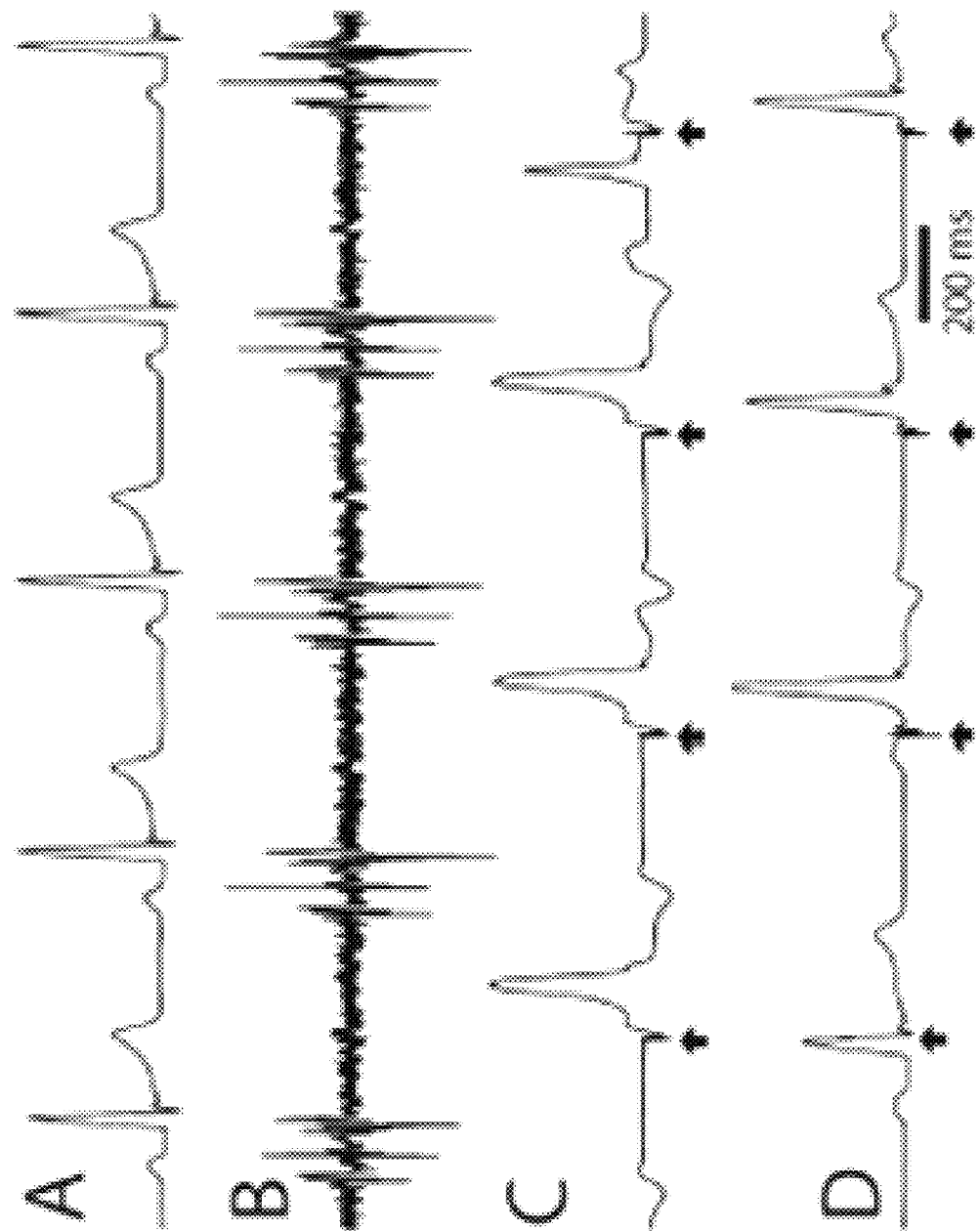
FIG. 14 illustrates paraHisian pacing in an intact dog heart. (A) Lead II surface ECG temporally aligned with (B) a bipolar mapping catheter positioned on the His bundle. (C) The ECG during pacing (arrows) with 13 mA shows three captured beats with wide QRS complexes and one sinus beat. (D) The ECG shows a sinus beat followed by three narrow complex QRS paced beats (arrows show 20 mA pacing artifact) during His bundle capture.

Experiments were conducted in three isolated rabbit hearts in which an 8×8 array was placed over the His bundle while another 4×4 array was placed on the RV free wall endocardium. The His bundle signal was input into a microcontroller (see FIG. 9), and pacing pulses were delivered at 90% of the His VF cycle length (see FIG. 13). In early VF, pacing did not result in capture. After pacing for 20 cycles, 1:1 capture of the His, Purkinje, and working myocardium was achieved. Upon termination of pacing, VF was terminated. This effect was achieved in three rabbit experiments. While regional capture was observed with epicardial pacing in two experiments (see FIG. 9), VF was not terminated with the termination of pacing. These promising experiments demonstrate evidence that His-Purkinje pacing during VF may be an effective treatment for VF cardioversion where ATP pacing of the ventricular myocardium is ineffective.

Example 3: Technique for Delivering Low-Energy Pacing Trains to the Purkinje System During VF to Terminate Fibrillation Direct pacing of the Purkinje system has proven difficult until recent improvements in steerable sheaths and catheters have become available. The Select Secure 3830 ventricular lead and the Select Site deflectable sheath (Medtronic, Inc.) is gaining acceptance as a feasible catheter for chronic His bundle pacing. While this approach has not been used for defibrillation, His bundle pacing has led to improved ventricular synchrony and cardiac output than patients with biventricular cardiac resynchronization therapy.

Algorithms for detection of tachycardia cycle lengths and ATP protocols are a standard feature in commercially available ICDs. Incorporation of multi-pulse or high frequency pulse trains to commercial devices likely will not require significant changes to hardware. The addition of a His-bundle lead to current ICDs may be accomplished by current CRT devices with a His-bundle pacing lead in place of a left ventricular lead.

As discussed previously, ICD patients with HF and associated pathologies may affect the efficacy of His-Purkinje pacing during VF.

Example 4

Ventricular fibrillation (VF) is an important cause of sudden cardiac death (SCD), which is responsible for approximately half of cardiac mortality. Implantable cardioverter defibrillators (ICDs) are now an established therapy for fatal ventricular tachyarrhythmia. However, large shocks may cause tissue damage and increase the risk of death. Thus, numerous defibrillation techniques have been studied to lower the energy required for cardioversion.

Some published studies have demonstrated that the Purkinje system (PS) is an important driver of VF activation in the maintenance of long duration VF (LDVF) (VF>2 min). PS activity was present in 84% of fibrillatory wave fronts during induced VF in dog isolated hearts and was responsible for driving the rapid activation rate during LDVF. Also, the PS has the same or shorter action potential duration (APD) and refractory periods than cardiomyocytes under rapid pacing rates, which suggests that the PS may have an excitable gap during VF. Thus, it is likely that appropriately timed pacing pulses in the PS can conduct through Purkinje-muscular junction (PMJ) and capture a large region of the working myocardium (WM) in VF. There have been modeling and small animal heart studies that suggest that stimulating PS during arrhythmias may lead to termination of the arrhythmias or reduction in energy required for termination. However, there has been lack of a clinically relevant method for stimulating PS in vivo.

Recently, a study was published that also has shown that during prolonged VF, the His bundle exhibits similar activation patterns as the PS. This suggests that the His and the PS remain electrically linked during VF and that pacing and capture of His may lead to capture of the PS during VF. However it is unclear whether the APD and refractory periods of the His have the similar electrophysiological properties with the Purkinje fibers that can be used as a target for interventional therapy.

Nine New Zealand white rabbits (weight of 2-4 kg) of either sex were anesthetized using intramuscular injections of 30 mg/kg ketamine and 5 mg/kg xylazine, followed by intravenous injections of 10 mg/kg ketamine, 3 mg/kg xylazine and 500 IU of heparin. After a median sternotomy, the hearts were excised and isolated rapidly in 4° C. Tyrode's solution, and then were Langendorff-perfused with 37° C. Tyrode's solution. The perfusion pressure was maintained at 60 to 70 mmHg. The hearts were also superfused by warm Tyrode's solution, with temperature maintained at 37±0.5° C. The composition of Tyrode's solution (in mM) was 130 NaCl, 1.2 NaH2PO4, 1 MgCl2, 4 KCl, 1.8 CaCl2, 24 NaHCO$_3$, 11.2 Glucose, and 0.04 g/L bovine albumin and it was oxygenated with O2 and CO2 to maintain a pH of 7.4±0.05. The excitation-contraction uncoupler Blebbistatin (10 mM/L; Calbiochem®, EMD Biosciences, Inc. La Jolla, Calif.) was added to Tyrode's solution to suppress motion artifacts in the recordings.

Figure 15:
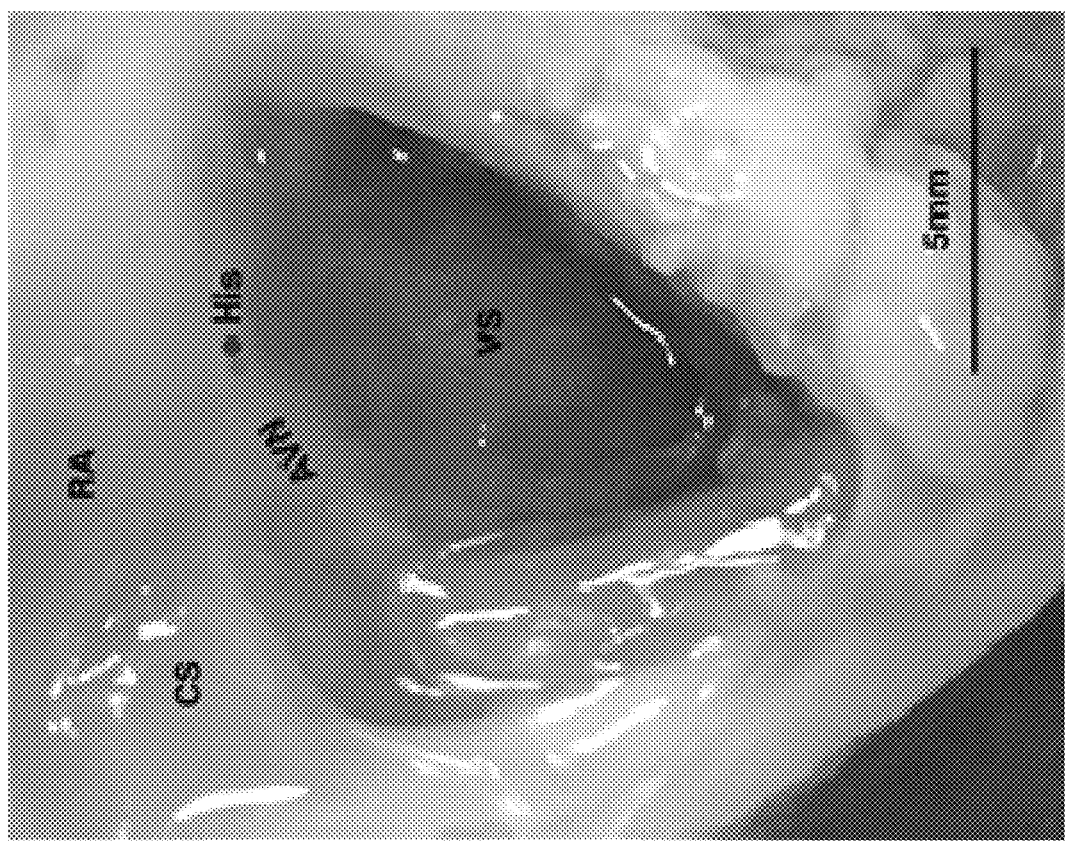
FIG. 15 is a photograph of the experimental rabbit heart showing the anatomical landmarks and the impalement sites. CS, coronary sinus; AVN, atrioventricular node; His, His bundle; RA, right atrium; VS, ventricular septum. Green dot indicates the recording site of the bipolar electrode. Action potentials were recorded from the His bundle (blue dot) and endocardium (red dot), respectively.
Figure 16:
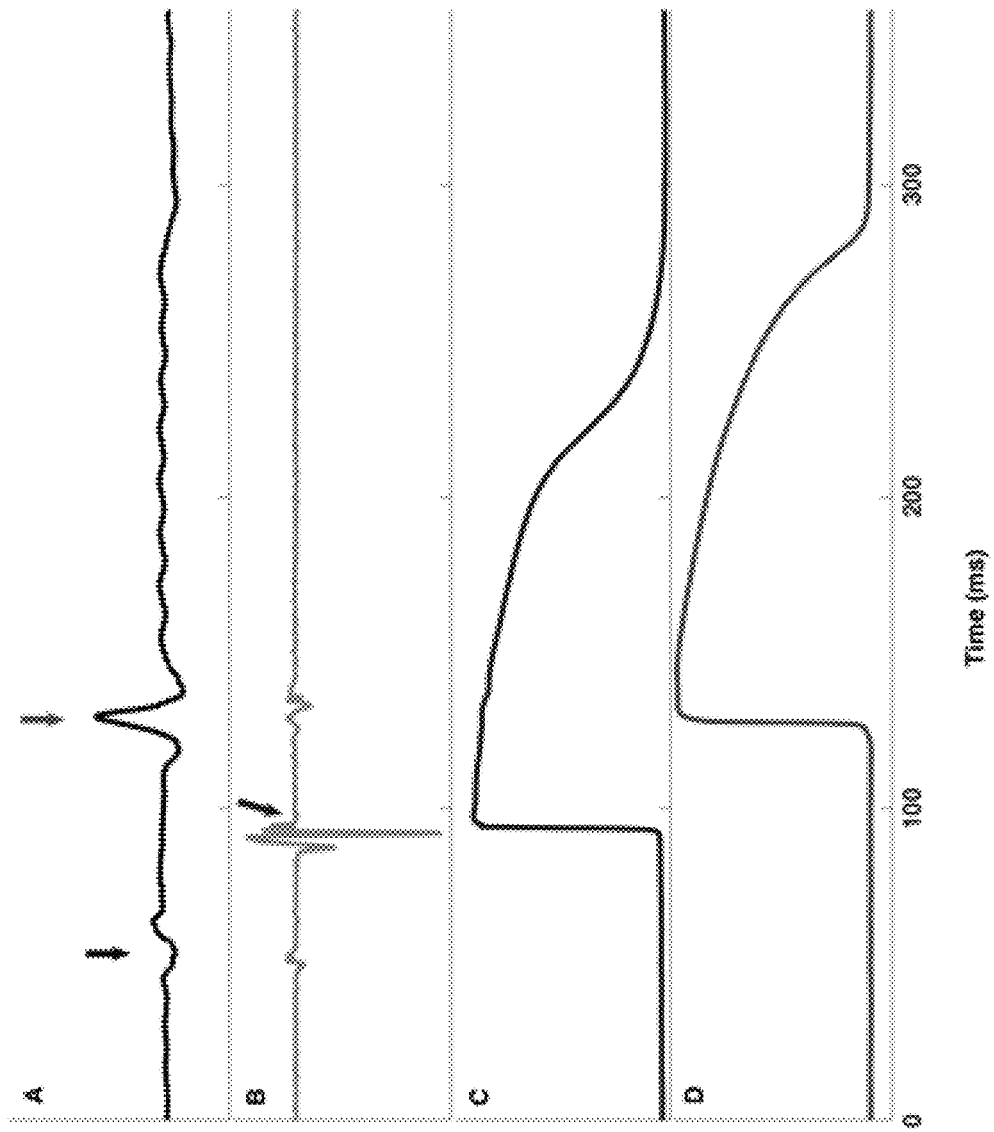
FIG. 16 is a graphical illustration of an example of the pseudo ECG (A), the bipolar electrogram (B) and microelectrode recordings of the His bundle (C) and the adjacent working myocardium (D). In the pseudo ECG panel, the first signal (black arrowed) is P wave and the second one (red arrow) is QRS wave. Panel B is the derivatives of the bipolar electrogram signals. The first and third deflections in panel B are temporally aligned with the P and QRS wave in panel A and the second deflection (green arrow) is the His bundle signal.

The right atrium was removed to expose the high right ventricular septum and His, as shown in FIG. 15. A bipolar electrode was placed on the His for signal discrimination and pacing. Two standard glass microelectrodes (tip resistance, 1 to 5 MΩ, filled with 3 mol/L KCl) were used to record the intracellular action potential (AP) from the His and the right ventricular septal endocardium simultaneously. One microelectrode impaled the His bundle within 2 mm of the bipolar electrode, which was used to verify that the action potential (AP) aligned with the His signal in the bipolar electrode. The other microelectrode recorded the WM signal (Endo group) within 10 mm of the His impalement site. An Ag—AgCl reference electrode for the intracellular recording electrode was placed in the perfusate. APs were recorded with DC coupling as the difference in voltage between the intracellular microelectrode and the extracellular Ag—AgCl reference electrode. The signals were acquired by an Axoclamp 900A amplifier (Axon Instruments, USA). Also, another three electrodes were placed in the perfusate to calculate pseudo-ECG. All the signals were recorded and monitored in real time using LabChart® software through a Powerlab 16/30 system (AD Instruments, Colorado Springs, Colo., USA) (FIG. 16).

Figure 17:
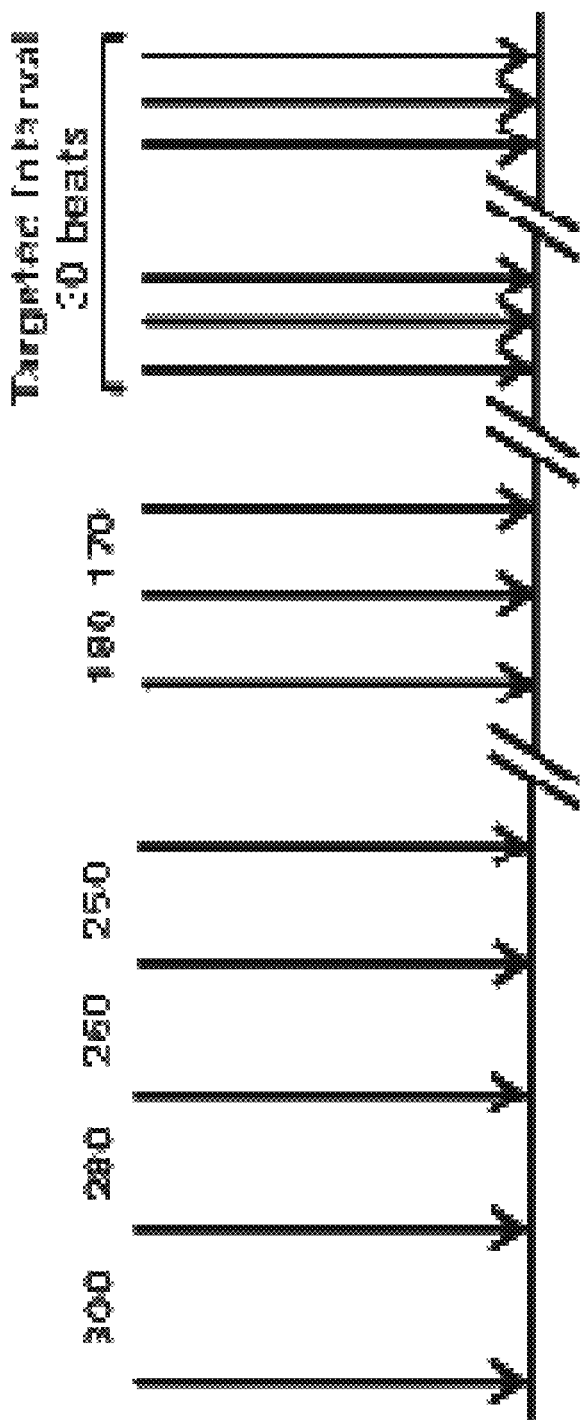
FIG. 17 illustrates a decremented-pacing protocol for measuring restitution properties. The initial interval was 300 ms and was decremented to 260 ms by 20-ms steps. Below 260 ms, it was reduced in 10-ms steps to the target interval, and thereafter kept at the target interval for 30 beats. Each cycle length was in ms.

Electrical pulses of 0.2 ms duration and twice diastolic threshold were delivered through the bipolar electrode placed on the His. A steady-state pacing protocol used as in a previously published study was used to determine the restitution characteristics. The S1-S1 interval was initially 300 ms and was progressively decreased to 260 ms by 20-ms steps, and then was reduced in 10-ms steps to the target interval, and thereafter kept at the target interval for 30 beats (FIG. 17). After finishing the restitution curve, the same protocol was used to pace from the ventricular apex to determine if capture of the WM was lost at the same cycle length (CL) with the one paced from the His bundle.

The data were selected if there was a stable microelectrode recording and the last 10 beats of the 30 beats at each pacing CL were analyzed. The APD was measured using LabChart® software at 90% repolarization (APD90). The diastolic interval (DI) was defined as the interval from the end of the repolarization time of the previous beat to the activation time of the next beat. The confirmative analysis focused on comparing if the relationship between APD and DI are the same for the His bundle and working myocardium. The non-linear relationship between APD and DI (ms) was assumed to be as follows.

$$y = \alpha - \beta e^{-x/\tau} \qquad (1)$$

where y denotes the value of APD and x for the value of DI, and $\alpha$, $\beta$ and $\tau$ are parameter coefficients being estimated from the data. It was assumed that both His and Endo shared the same parameters for $\alpha$, $\beta$ and $\tau$ in the above nonlinear model (1) and fit a common-parameter model. Then, the non-linear model was fit assuming that each of the parameters, $\alpha$, $\beta$ and $\tau$, was different between the His and the Endo group. A global F-test was used to examine if two models (the model assuming common parameters and the model assuming different parameters) were statistically significantly different from each other. If the F-test indicated that the two models were significantly different, then the relationship between APD and DI (or between APD and CL) was significantly different across the two (His and Endo) groups. The non-linear model was fit (1) again and re-parametrized the model so that we can check which of the three parameters ($\alpha$, $\beta$ and $\tau$) were significantly different between the His and Endo group. If any of the parameters were found significantly different between the His and Endo group, a separate coefficient for that parameter was estimated for the His and the Endo group. Otherwise, if a parameter was found to be not significantly different between the His and Endo group, the same coefficient was used for that parameter for both groups. The final model included the common parameter(s) and the separate parameter(s) based on the above processes. If the global F-test indicated that the difference between the common parameters model and the separate parameters model was not significantly different from each other, the relationship between APD and DI was the same for the two groups, and the common parameter model was served as the final model.

For the relationship between APD and CL, either a linear or non-linear relationship was developed by previous studies. Hence, a derived outcome was used, the area under the curve (AUC), for comparing between groups. The AUC was calculated using the two-way curve with APD on the y-axis and CL on the x-axis with the same range of CL for all animals within His and Endo groups. The AUC was calculated by summing up the areas of trapezoids generated by projecting each data point of ADP and CL pair onto the x-axis (a triangular shape was obtained for the area from point (0, 0) to the pair of ADP and the minimal CL). Although AUCs are continuous measurements, due to fact that the AUCs are not normally distributed for both Endo and His groups a Wilcoxon signed rank test was used for comparing AUCs between His and Endo groups.

All statistical analyses were performed using SAS (SAS Inc., Cary, N.C., USA) version 9.4. Test results with p-values <0.05 were considered as statistically significant.

Figure 18:
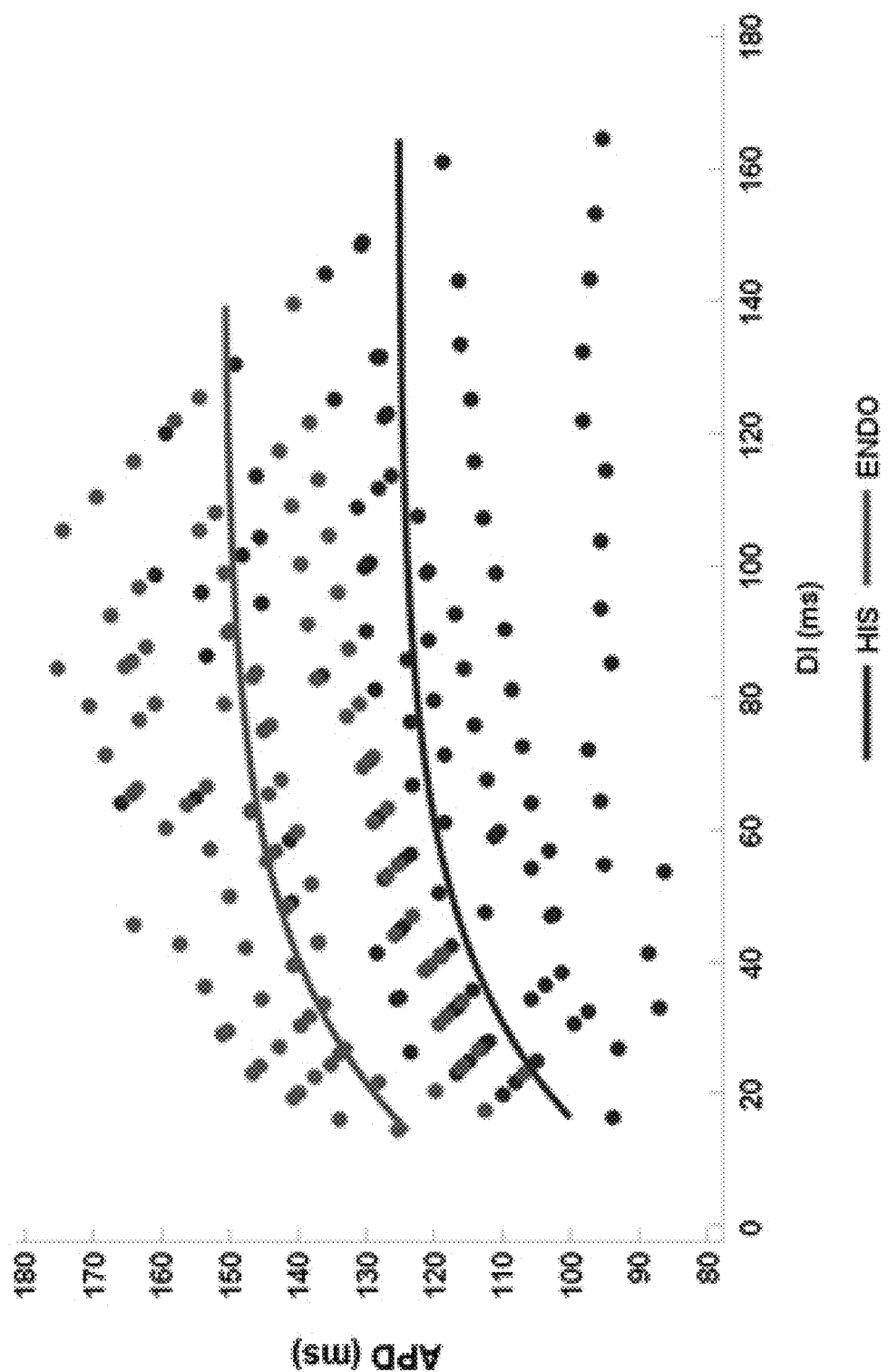
FIG. 18 is a scatterplot of ADP versus DI with fitted lines. The blue dots and line denote the data points and the fitted line for the His group, and the red dots and lines for the Endo group.

FIG. 18 presents the scatterplot of APD versus DI for both His and Endo groups with the fitted restitution curves. Both common-parameter and separate-parameter models are fitted for APD versus DI among the His and Endo groups. The global F-test indicated that the two models are statistically significantly different (p<0.000001). By examining each of the three parameters in the non-linear model, it was discovered that only the α parameter is significantly different between the two groups. The expected difference is 31.21 (95% CI: 15.33 to 47.09, p<0.0001), with the Endo groups having a larger value. Thus, the relationship between APD and DI are different across His and Endo groups.

Figure 19:
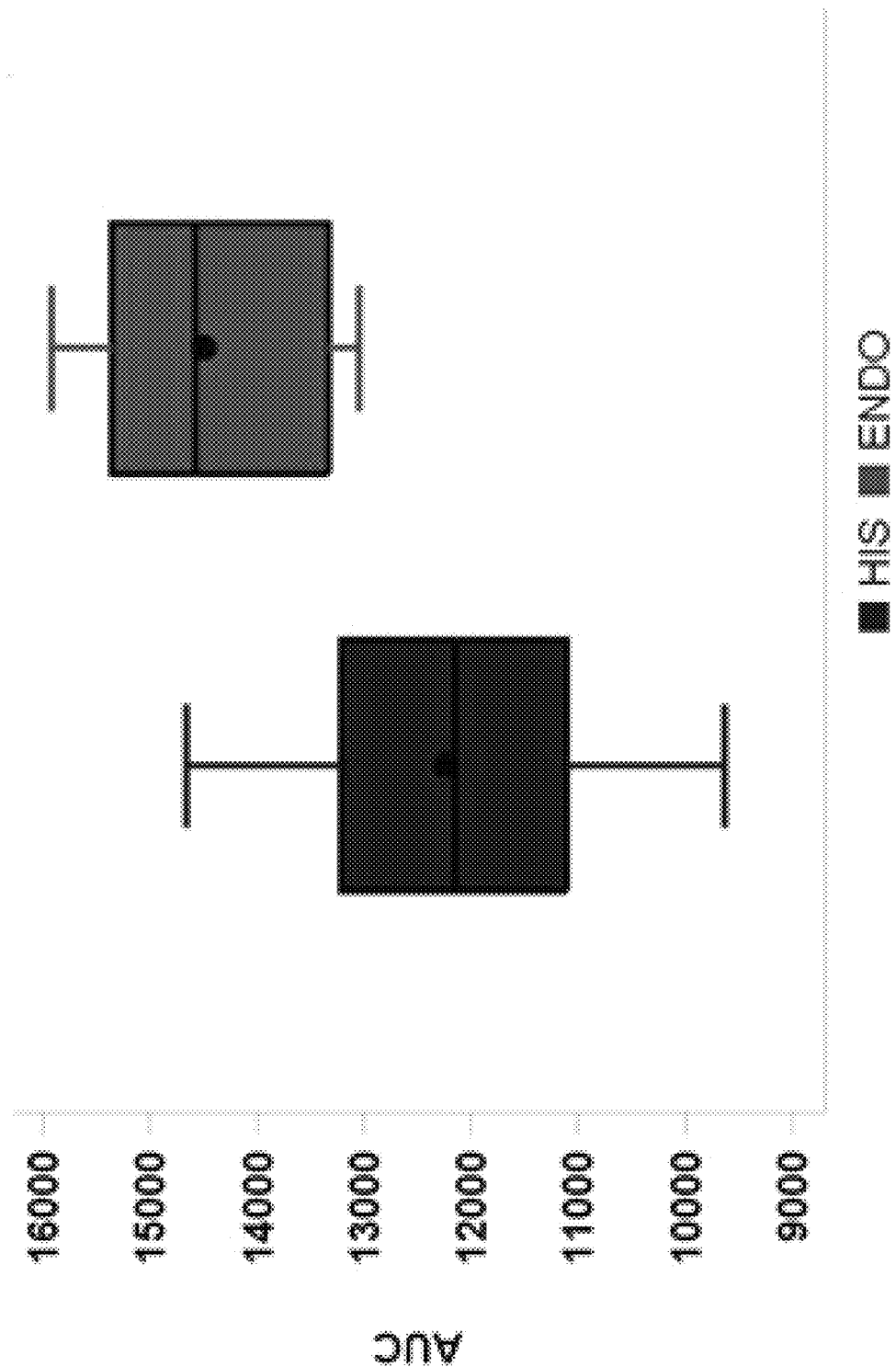
FIG. 19 is a boxplot of AUC. The blue boxplot is for the His group, and the red one is for the Endo group.

The Wilcoxon signed rank test was performed to compare the paired AUCs between His and Endo group under the null hypothesis that the AUCs under both groups are equal. At the 0.05 test level, this null hypothesis was rejected (p=0.018) and it was concluded that the Endo and His groups have statistically significantly different AUCs that describe the relationship between APD and CL (FIG. 19).

Figure 20:
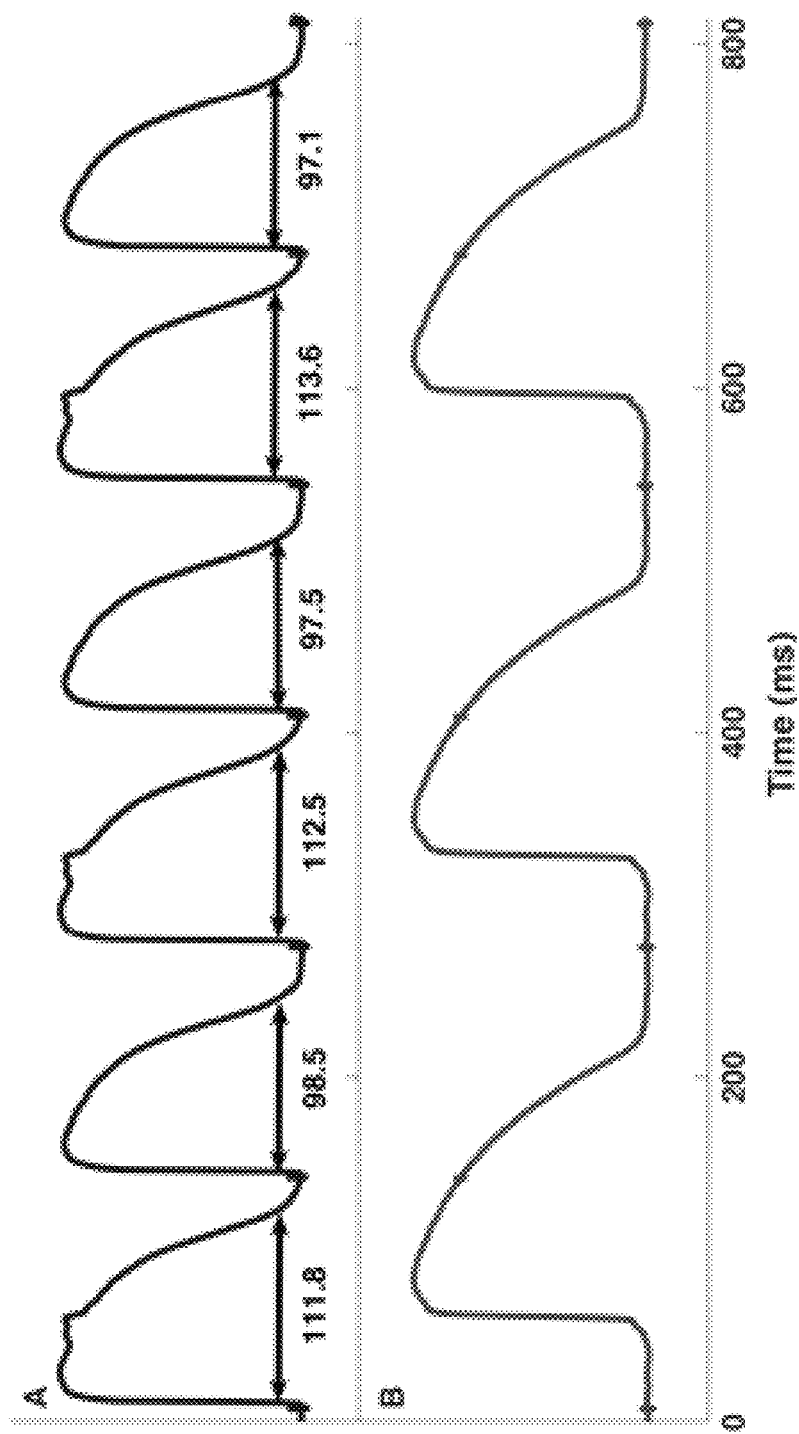
FIG. 20 illustrates action potential duration alternans continuously recorded in the His bundle (A) and 2:1 block in the adjacent working myocardium (B) at the cycle length of 130 ms pacing from the His bundle. The spikes in the recordings are the pacing artifacts. In panel A, the APD90 of the His bundle alternated in a long-short pattern. The long APDs ranged from 111.8 ms to 113.6 ms, while the short ones ranged from 97.1 ms to 98.5 ms. The working myocardium lost one to one capture when the His bundle had alternans.
Figure 21:
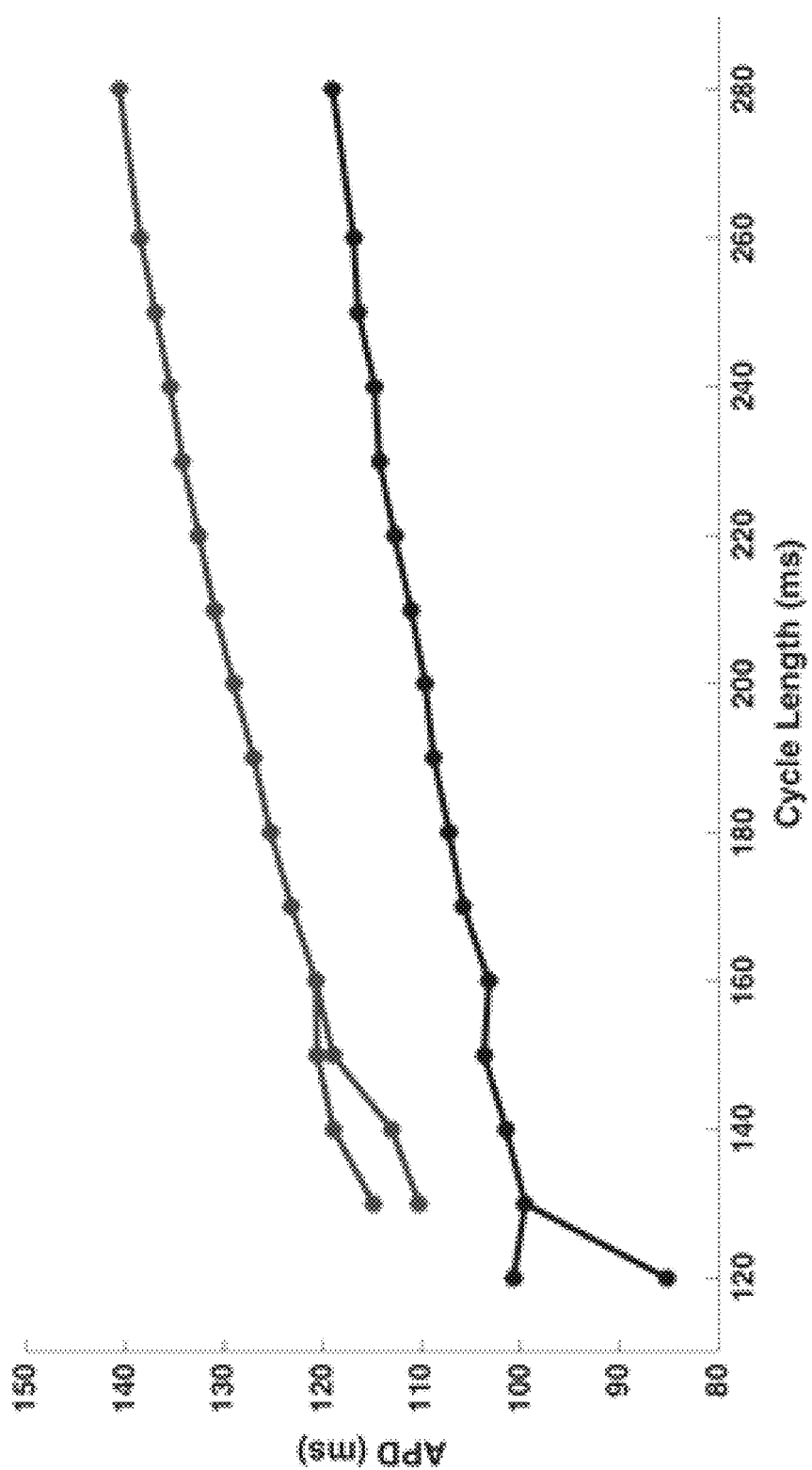
FIG. 21 illustrates action potential durations (APD90) during dynamic pacing in the His bundle (blue dots and curves) and working myocardium (red dots and curves). As cycle length progressively shortened, a transition from 1:1 capture to 2:1 block with alternation between long and short action potentials occurred.

During dynamic pacing, as the target interval closed to the CL where His or WM developed 2:1 block, the onset of APD alternans usually occurred. The His alternans developed in 7 of the 9 animals (77.8%). Among these seven animals that had His alternans, four rabbits also displayed WM alternans. There was another one animal (11.1%) that had only WM alternans with no His alternans. The His alternans developed at an average CL of 134.2±13.1 ms. Compared with the His alternans, the WM alternans happened at longer CL (148.3±13.3 ms, p<0.05). Similar to alternans, 2:1 block also developed at shorter CL in His than in WM (130.0±10.0 vs. 145.6±14.2 ms, P<0.01). Furthermore, it was discovered that most alternans of His occurred when the WM had 2:1 block (9 out of 12, 75.0%). FIGS. 20 and 21 showed the APD90 during dynamic pacing in His and WM from one animal. The WM had alternans and 2:1 block at 150 ms and 120 ms respectively, while the alternans and 2:1 block of His happened at 120 ms and 110 ms respectively.

The main findings from this study are as follows: 1) The His can be captured at shorter cycle lengths than the WM, 2) The APD of the His is shorter than the APD of the WM, and 3) Alternans develop in the His at short cycle lengths with His pacing when 2:1 conduction block occurs in the WM.

As mentioned previously, the PS plays a significant role as a driver of the rapid activation rates of VF, particularly after the first 2-3 minutes of VF. An excitable gap exists in the WM during VF20 and the results of this study demonstrate that the APD of His is shorter than that of the WM across a broad range of CLs. This is consistent with the theory that an excitable gap may exist in His during VF. For a pacing therapy to be successful at capturing His and potentially to spread to the WM through the specialized conduction system, an excitable gap in His would be necessary.

Alternans have been shown to be related to conduction block and potentially to arrhythmia onset. Because of the slow propagation and long refractory period of the atrioventricular node (AVN), alternans in the AVN node and phenomenon such as Winkebache conduction through the AVN node are well documented. This may be the first documentation of consistent alternans generation during His bundle pacing. The results showed that the ventricular alternans developed in longer CL than His alternans, which suggested that the ventricle lost 1:1 capture in longer CL than the His. In other words, when His had alternans, 2:1 block occurred in the WM. As pacing CL decreased, calcium transient alternans may happen, which will cause repolarization alternans in His. As a result, the APD will alternate in a long-short pattern. For the shorter AP in His, less current (the source) was generated, which may be not sufficient enough to bring the adjacent repolarized tissue (the sink) to its activation threshold, and propagation will fail as the source-sink mismatch is too large. However, there is another viewpoint that the alternans might be due to electrotonic coupling with a nearby area showing 2:1 block, resulting in "secondary" alternans. Strong electrical communication via gap junction with other cells may cause a smoothing of the Ca2+ signal over many cells, preventing alternans (voltage-Ca2+ feedback). There are also some studies that demonstrated that partial gap junction inhibition did have a strong effect on Ca2+ transient alternans, significantly increasing the occurrence and intensity. From these results, it was difficult to determine definitively the relationship between the His alternas and ventricular 2:1 block. Thus, further studies are needed to explore the mechanism of the His alternans.

The APD of the His was significantly shorter than that of the WM, which may provide the opportunity for delivering critically timed pulses to the His and capturing both the specialized conduction system and the WM to disrupt arrhythmias such as ventricular tachycardia or ventricular fibrillation with short cycle lengths.

Various features of the invention are set forth in the following claims.

What is claimed is:
1. An implantable cardioverter-defibrillator comprising:
a power source;
a controller, powered by the power source, including an electronic processor, a memory, and a pulse generator;
a His-bundle lead coupled to the controller and an electrode that is configured to make in electrical contact with the His-bundle of a patient's heart;
a capacitor circuit including a capacitor configured to deliver a defibrillation shock to the His-bundle; and
a sensing lead coupled to the controller and configured to make in electrical communication with the patient's heart, the sensing lead configured to detect electrical signals generated by the patient's heart, and
wherein the controller is configured to
receive the electrical signals provided by the sensing lead,
process the electrical signals to determine if ventricular fibrillation is present,
if ventricular fibrillation is detected on the electrical signals,
determine a cycle length of the ventricular fibrillation and a set of pacing pulse characteristics for the ventricular fibrillation, wherein the set of pacing pulse characteristics includes at least a number of pulses, pulse duration, pulse cycle length, current, and voltage based on an average of the cycle length of the ventricular fibrillation, while transmitting a signal to the capacitor circuit to charge the capacitor, transmit instructions to the pulse generator to deliver a pulsed defibrillation signal in accordance with the set of pacing pulse characteristics to the electrode to terminate the ventricular fibrillation, decrease speed of delivery of the pulsed defibrillation signal to a normal sinus rate, process the electrical signals to determine if ventricular fibrillation is present after transmission of the pulsed defibrillation signal to the electrode, if ventricular fibrillation remains present in the electrical signals, transmit a signal to the capacitor circuit to deliver a defibrillation shock to the electrode, if ventricular fibrillation is no longer present in the electrical signals, transmit a signal to the capacitor circuit to discharge the capacitor.

2. The implantable cardioverter defibrillator of claim 1, wherein the pulsed defibrillation signal is based on a cycle length of the ventricular fibrillation.

3. The implantable cardioverter defibrillator of claim 2, wherein the pulsed defibrillation signal provides 10-30 pacing pulses at 80%-105% of the cycle length of the ventricular fibrillation.

4. The implantable cardioverter defibrillator of claim 1, further comprising a detector circuit coupled to the sensing lead.

5. A method for ventricular defibrillation, the method comprising:

detecting the presence of ventricular fibrillation in a patient via an implantable cardioverter-defibrillator including a sensing lead and a controller electrically coupled to an electrode that is in electrical communication with a His-bundle of a patient's heart;

determining, via the controller, a pulsed defibrillation signal based on a cycle length of the ventricular fibrillation and a set of pacing pulse characteristics for the ventricular fibrillation, wherein the set of pacing pulse characteristics includes at least a number of pulses, pulse duration, pulse cycle length, current, and voltage based on an average of the cycle length of the ventricular fibrillation;

transmitting a signal to a capacitor circuit in the implantable cardioverter-defibrillator to charge a capacitor;

transmitting a signal, via the controller, to a pulse generator to deliver the pulsed defibrillation signal to the electrode transmitting a signal, via the controller, to the pulse generator to decrease speed of delivery of the pulsed defibrillation signal to a normal sinus rate, detecting, via the controller, if ventricular fibrillation is present after transmitting the pulsed defibrillation signal to the electrode, if ventricular fibrillation remains present, transmitting a signal to the capacitor circuit to deliver a defibrillation shock to the electrode, if ventricular fibrillation is no longer present, transmitting a signal to the capacitor circuit to discharge the capacitor.

6. The method of claim 5, wherein the ventricular fibrillation characteristic is based on a cycle length of the ventricular fibrillation signal.

7. The method of claim 6, wherein the pulsed defibrillation signal provides 10-30 pacing pulses at 80%-105% of the cycle length of the ventricular fibrillation.

8. The method of claim 6, wherein the signal includes about 10 to about 30 small pulses at about 90% of the cycle length.

* * * * *